(12) United States Patent
Patton et al.

(10) Patent No.: US 11,568,978 B2
(45) Date of Patent: Jan. 31, 2023

(54) DENTAL LASER INTERFACE SYSTEM AND METHOD

(71) Applicant: Biolase, Inc., Irvine, CA (US)

(72) Inventors: Douglas Patton, Costa Mesa, CA (US); Dmitri Boutoussov, Dana Point, CA (US); Christopher J. Walinski, Huntington Beach, CA (US); Richard Jackson, Trabuco Canyon, CA (US)

(73) Assignee: BIOLASE, INC., Irvine, CA (US)

( * ) Notice: Subject to any disclaimer, the term of this patent is extended or adjusted under 35 U.S.C. 154(b) by 0 days.

(21) Appl. No.: 17/568,124

(22) Filed: Jan. 4, 2022

(65) Prior Publication Data

US 2022/0208334 A1 Jun. 30, 2022

Related U.S. Application Data

(63) Continuation of application No. 17/104,590, filed on Nov. 25, 2020, now Pat. No. 11,250,941, which is a (Continued)

(51) Int. Cl.
*G16H 20/40* (2018.01)
*G06F 3/0482* (2013.01)
(Continued)

(52) U.S. Cl.
CPC ........... *G16H 20/40* (2018.01); *A61C 1/0007* (2013.01); *A61C 1/0046* (2013.01);
(Continued)

(58) Field of Classification Search
None
See application file for complete search history.

(56) References Cited

U.S. PATENT DOCUMENTS

| 5,676,387 A | 10/1997 | Kirkpatrick |
| 5,961,626 A | 10/1999 | Harrison et al. |

(Continued)

FOREIGN PATENT DOCUMENTS

| CN | 106456278 | 2/2017 |
| EP | 0597467 | 5/1994 |

(Continued)

OTHER PUBLICATIONS

Korean Intellectual Property Office; PCT Written Opinion of the International Searching Authority, Issued in connection to PCT/US2015/022093; dated Jun. 29, 2015; 6 pages; Korea.

(Continued)

*Primary Examiner* — Toan H Vu
(74) *Attorney, Agent, or Firm* — Greenberg Traurig, LLP

(57) ABSTRACT

Embodiments of the invention provide a system of controlling a dental laser system. The system can include a dental laser and a control system for controlling certain functions of the dental laser. A graphical user interface can be used to provide input to the control system. The graphical user interface can include a first display and an second display with selectable segments, and a menu navigation portion located adjacent the second display. Treatment categories, procedures or laser control options can be selected using the interface, and the interface can be updated based on data from the station.

18 Claims, 32 Drawing Sheets

Related U.S. Application Data continuation of application No. 15/866,173, filed on Jan. 9, 2018, now Pat. No. 10,877,630, which is a continuation of application No. 14/666,287, filed on Mar. 23, 2015, now Pat. No. 9,864,485.

(60) Provisional application No. 61/968,632, filed on Mar. 21, 2014.

(51) Int. Cl.
*G06F 3/04847* (2022.01)
*G06F 3/04842* (2022.01)
*A61C 1/00* (2006.01)
*G16H 40/63* (2018.01)

(52) U.S. Cl.
CPC ........ *G06F 3/0482* (2013.01); *G06F 3/04842* (2013.01); *G06F 3/04847* (2013.01); *G16H 40/63* (2018.01)

(56) References Cited

U.S. PATENT DOCUMENTS

| | | | |
|---|---|---|---|
| 6,030,222 A | 2/2000 | Tarver | |
| 6,081,895 A | 6/2000 | Harrison et al. | |
| 6,251,073 B1 | 6/2001 | Imran et al. | |
| 6,351,678 B1 * | 2/2002 | Borders | G16H 20/30 700/83 |
| 6,550,012 B1 | 4/2003 | Villa et al. | |
| 6,569,102 B2 | 5/2003 | Imran et al. | |
| 6,685,645 B1 | 2/2004 | McLaughlin et al. | |
| 6,733,455 B2 | 5/2004 | Mo et al. | |
| 6,773,399 B2 | 8/2004 | Xi et al. | |
| 6,793,653 B2 | 9/2004 | Sanchez et al. | |
| 6,896,658 B2 | 5/2005 | Ji et al. | |
| 6,936,008 B2 | 8/2005 | Tarakci et al. | |
| 6,997,876 B2 | 2/2006 | Mo et al. | |
| 7,022,075 B2 | 4/2006 | Grunwald et al. | |
| 7,238,157 B2 | 7/2007 | McLaughlin et al. | |
| 7,361,145 B2 | 4/2008 | Xi et al. | |
| 7,682,309 B2 | 3/2010 | Ji et al. | |
| 8,002,767 B2 | 8/2011 | Sanchez et al. | |
| 8,226,561 B2 | 7/2012 | McLaughlin et al. | |
| 8,496,474 B2 | 7/2013 | Chishti et al. | |
| 8,764,661 B2 | 1/2014 | McLaughlin et al. | |
| 8,679,018 B2 | 3/2014 | McLaughlin et al. | |
| 8,734,150 B2 | 5/2014 | Chishti et al. | |
| 8,939,891 B2 | 1/2015 | Sanchez et al. | |
| 9,864,485 B2 | 1/2018 | Patton | |
| 2002/0038088 A1 | 3/2002 | Imran et al. | |
| 2002/0138002 A1 | 9/2002 | Tarakci et al. | |
| 2002/0169378 A1 | 11/2002 | Mo et al. | |
| 2002/0173721 A1 | 11/2002 | Grunwald et al. | |
| 2003/0013959 A1 | 1/2003 | Grunwald et al. | |
| 2003/0078497 A1 | 4/2003 | Ji et al. | |
| 2003/0109857 A1 | 6/2003 | Sanchez et al. | |
| 2003/0195644 A1 * | 10/2003 | Borders | A61G 12/00 340/568.1 |
| 2003/0220573 A1 | 11/2003 | Imran et al. | |
| 2004/0024316 A1 | 2/2004 | Xi et al. | |
| 2004/0044295 A1 | 3/2004 | Reinert et al. | |
| 2004/0138569 A1 | 7/2004 | Grunwald et al. | |
| 2004/0147841 A1 | 7/2004 | McLaughlin et al. | |
| 2004/0169673 A1 * | 9/2004 | Crampe | A61B 34/20 600/300 |
| 2004/0199078 A1 | 10/2004 | Mo et al. | |
| 2004/0267138 A1 | 12/2004 | Xi et al. | |
| 2005/0041282 A1 * | 2/2005 | Rudolph | G02B 21/0012 359/368 |
| 2005/0043719 A1 | 2/2005 | Sanchez et al. | |
| 2005/0075703 A1 | 4/2005 | Larsen | |
| 2005/0131294 A1 | 6/2005 | Ji et al. | |
| 2006/0036178 A1 | 2/2006 | Tarakci et al. | |
| 2006/0100520 A1 | 5/2006 | Mo et al. | |
| 2006/0116578 A1 | 6/2006 | Grunwald et al. | |
| 2007/0103270 A1 | 5/2007 | Gmeinder et al. | |
| 2007/0213615 A1 | 9/2007 | McLaughlin et al. | |
| 2007/0239488 A1 * | 10/2007 | DeRosso | G16H 30/20 705/3 |
| 2008/0182220 A1 | 7/2008 | Chishti et al. | |
| 2008/0222569 A1 | 9/2008 | Champion et al. | |
| 2009/0187176 A1 | 7/2009 | Assa | |
| 2009/0225060 A1 | 9/2009 | Rizoiu et al. | |
| 2010/0082019 A1 | 4/2010 | Neev | |
| 2010/0268082 A1 | 10/2010 | McLaughlin et al. | |
| 2010/0268083 A1 | 10/2010 | McLaughlin et al. | |
| 2010/0281370 A1 * | 11/2010 | Rohaly | G06T 15/205 715/810 |
| 2010/0311028 A1 | 12/2010 | Bell, III et al. | |
| 2011/0301616 A1 | 12/2011 | Sanchez et al. | |
| 2012/0036434 A1 | 2/2012 | Oberstein | |
| 2012/0124520 A1 | 5/2012 | Samp | |
| 2013/0104071 A1 | 4/2013 | Boutoussov | |
| 2013/0145316 A1 | 6/2013 | Heo | |
| 2013/0219340 A1 | 8/2013 | Linge | |
| 2013/0302743 A1 | 11/2013 | Chishti et al. | |
| 2014/0047389 A1 | 2/2014 | Aarabi | |
| 2014/0059486 A1 | 2/2014 | Sasaki et al. | |
| 2014/0137042 A1 | 5/2014 | Du et al. | |
| 2014/0170588 A1 | 6/2014 | Miller | |
| 2014/0180463 A1 | 6/2014 | Chishti et al. | |
| 2014/0195979 A1 | 7/2014 | Branton et al. | |
| 2014/0272771 A1 | 9/2014 | Boutoussov et al. | |
| 2014/0363784 A1 | 12/2014 | Monty et al. | |
| 2014/0379356 A1 * | 12/2014 | Sachdeva | A61C 7/002 705/2 |
| 2015/0268803 A1 | 9/2015 | Patton | |

FOREIGN PATENT DOCUMENTS

| | | |
|---|---|---|
| EP | 36119345 | 1/2017 |
| WO | 2012/074918 | 6/2012 |
| WO | 2015/143456 | 9/2015 |

OTHER PUBLICATIONS

Korean Intellectual Property Office; PCT International Search Report, Issued in connection to PCT/US2015/022093; dated Jun. 29, 2015; 4 pages; Korea.

The International Bureau of WIPO; PCT International Preliminary Report on Patentability, Issued in connection to PCT/US2015/022093; dated Sep. 21, 2016; 7 pages; Switzerland.

European Patent Office; Extended European Search Reprot, Issued in connection to EP15765014.4; dated Nov. 15, 2017; 7 pages; Europe.

* cited by examiner

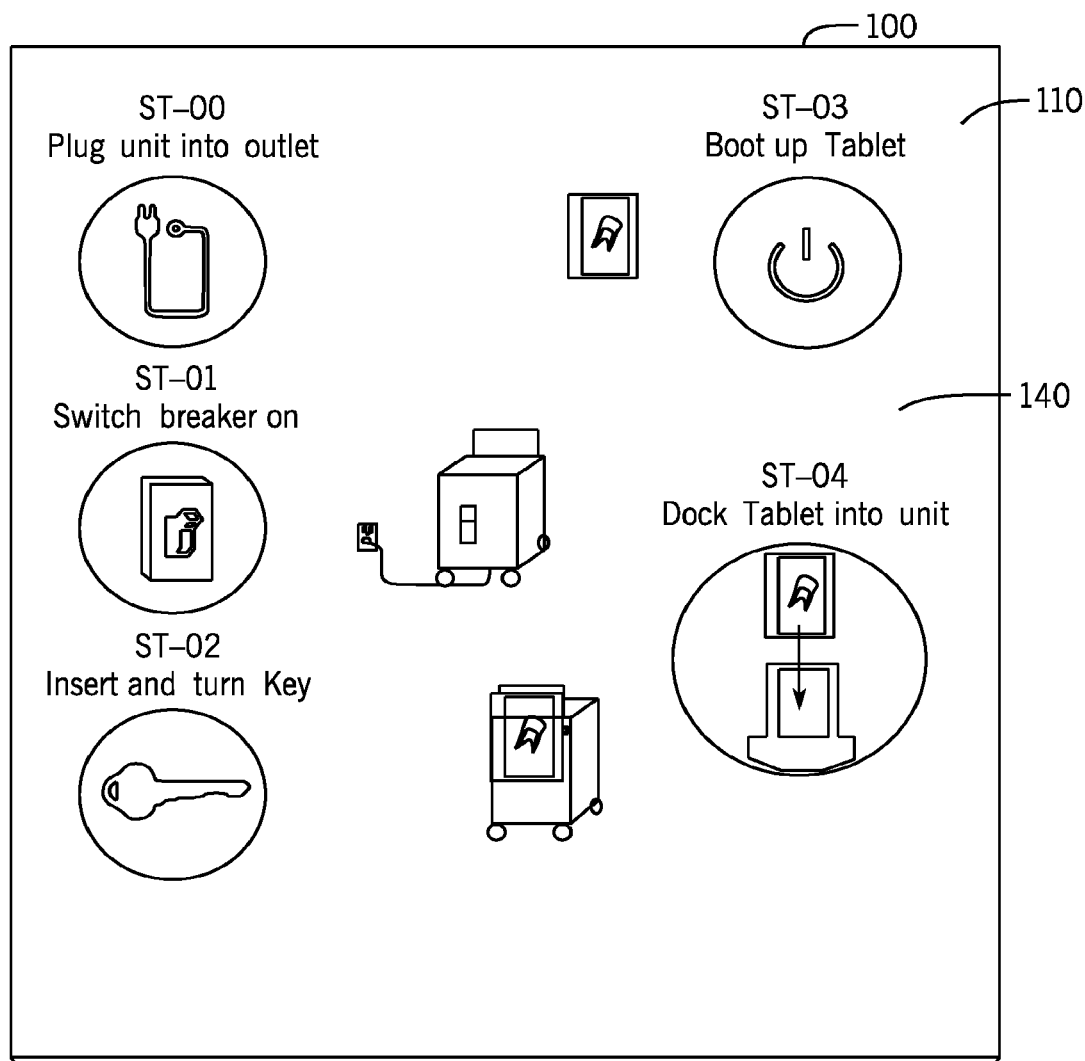
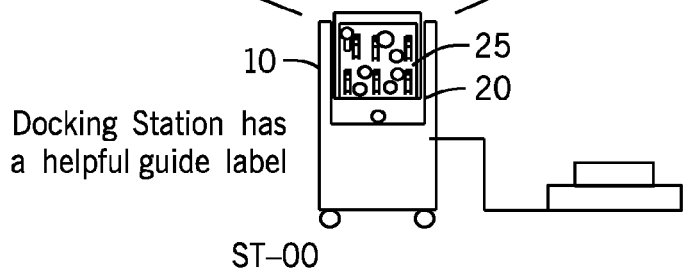
FIG. 3

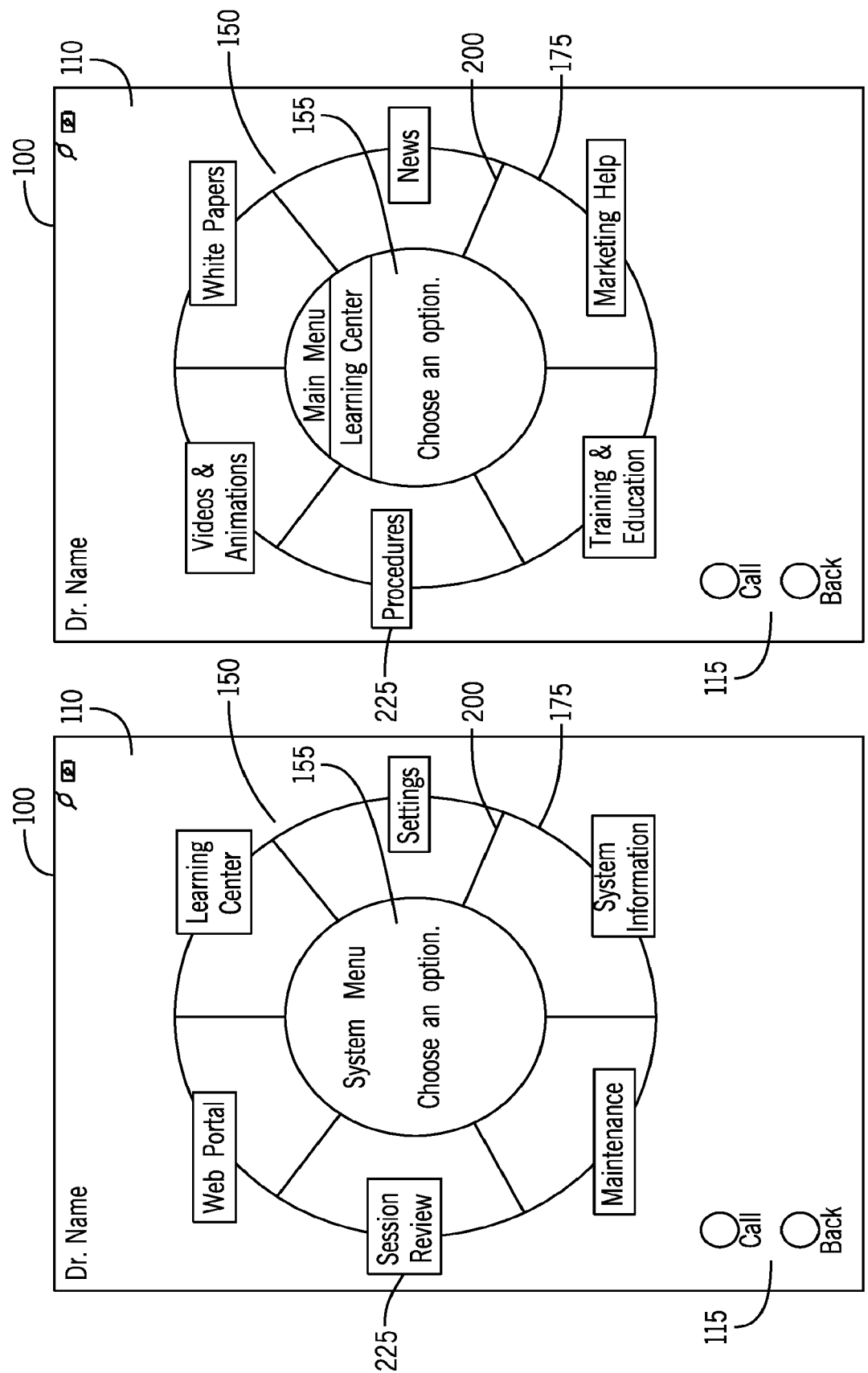

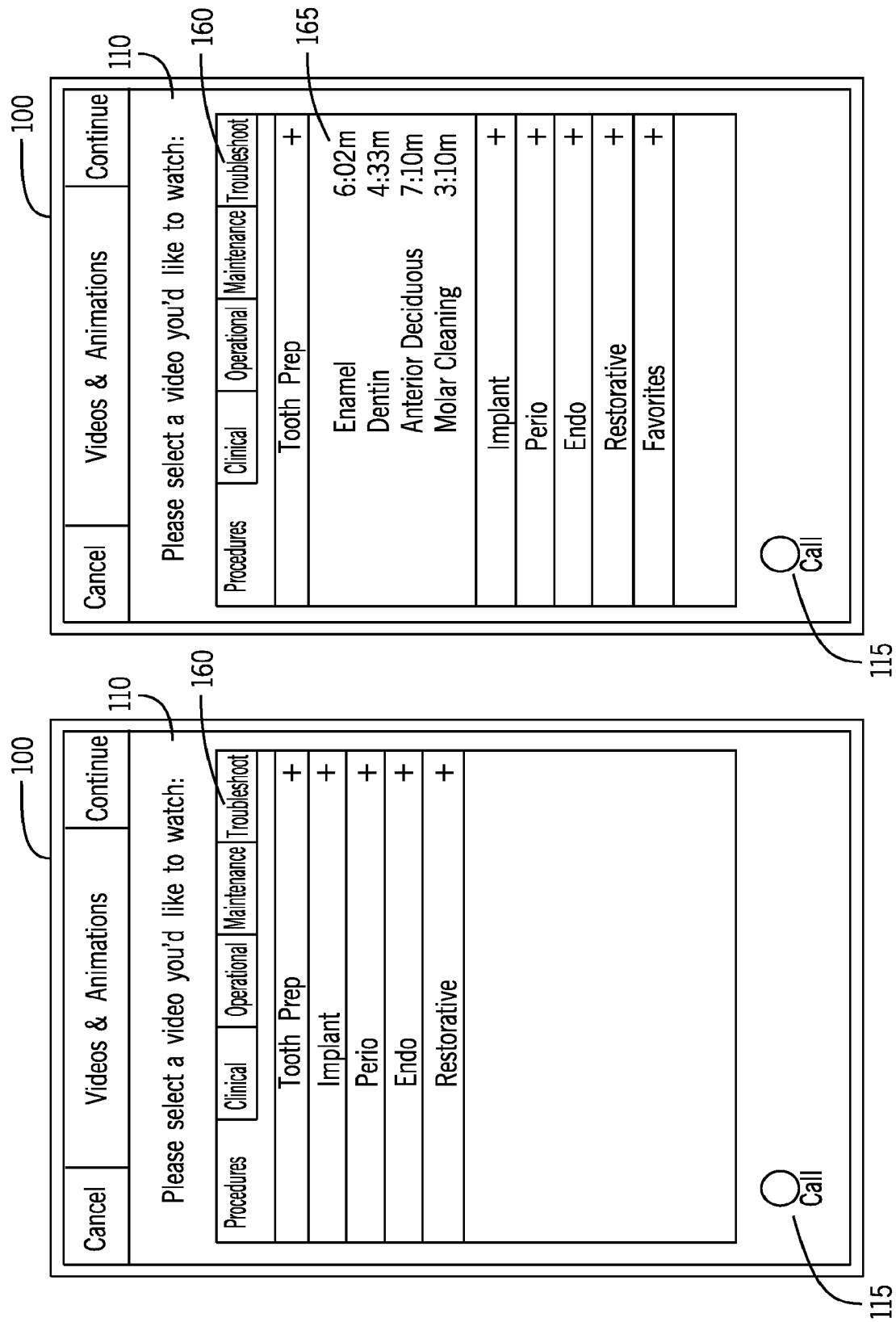

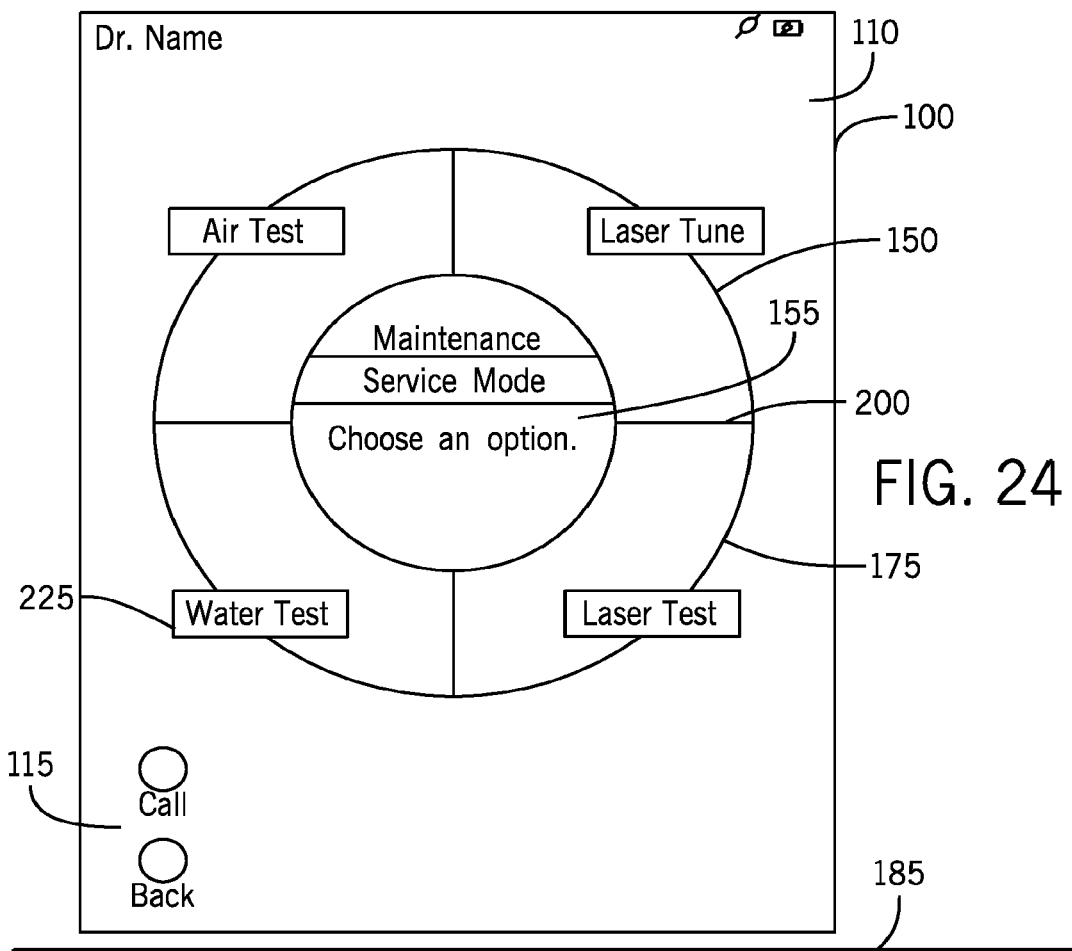
FIG. 24
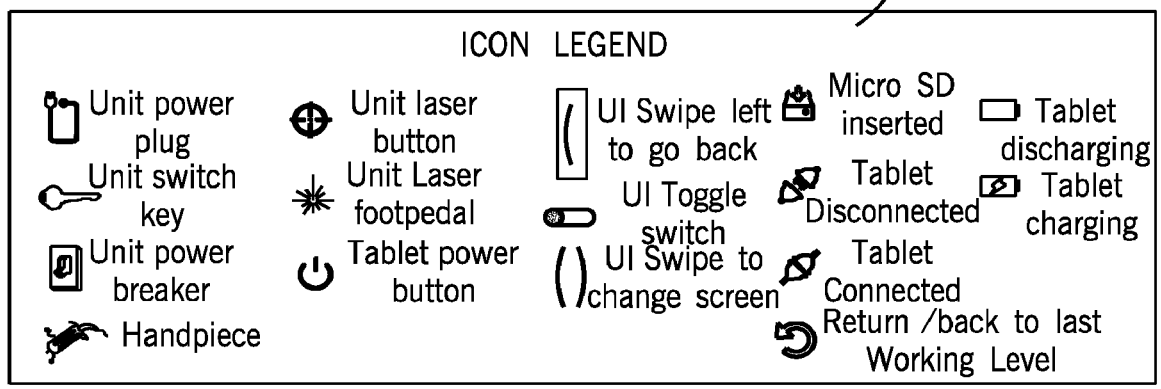
FIG. 25
| HANDPIECES & TIPS | | | | |
|---|---|---|---|---|
| Handpieces | Sapphire Tips | | Z-Tips (Zip Tips) | |
| Gold | S75 | C1 | Z2 | Z4 |
| Silver | G6 | C6 | Z3 | Z5 |
| Turbo | T4 | C3 | | Z6 |
| Standard | | | | |
FIG. 26

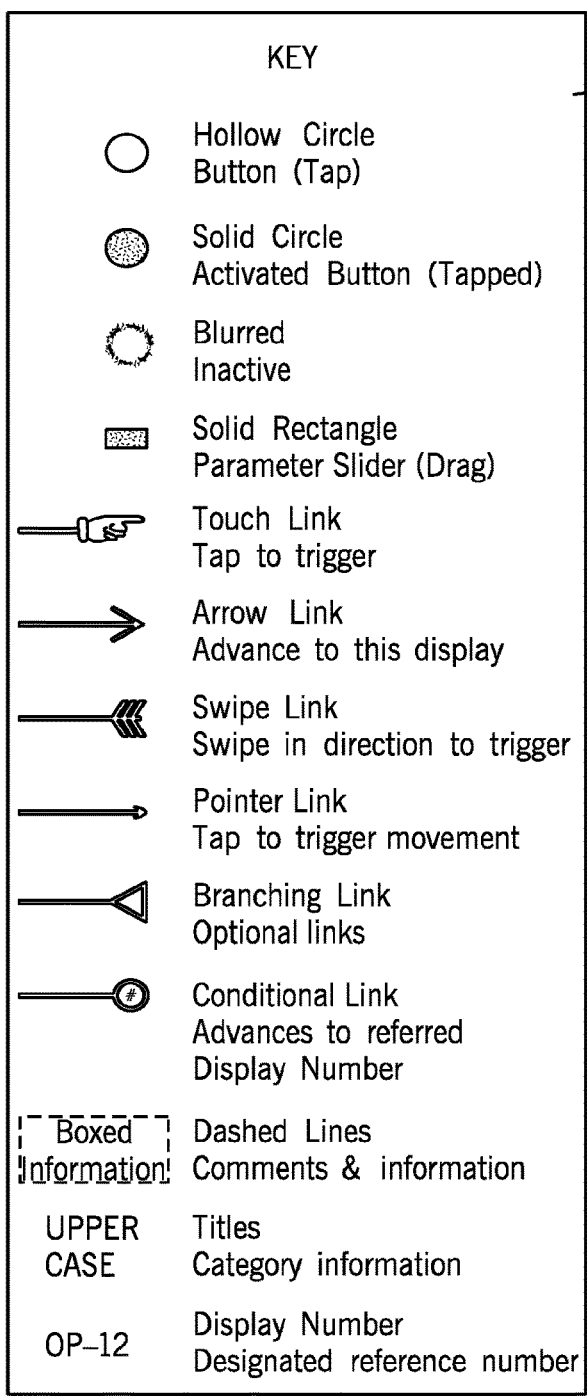

There are 2 modalities of inputs for saving.
1. Circle Pie– press hold for 2 seconds (modal popup in center) saves the step in the circle pie.

☆ Star: Default Settings

🔓 Unlocked: Modified, ready to save

🔒 Locked: Modified, saved.

2. Save button (denoted by heart icon) auto saves to favorite as a procedure in favorites (even if it was a step.)

♥ Full Heart: Add to Favorites

♡ Heart outline: Already added.

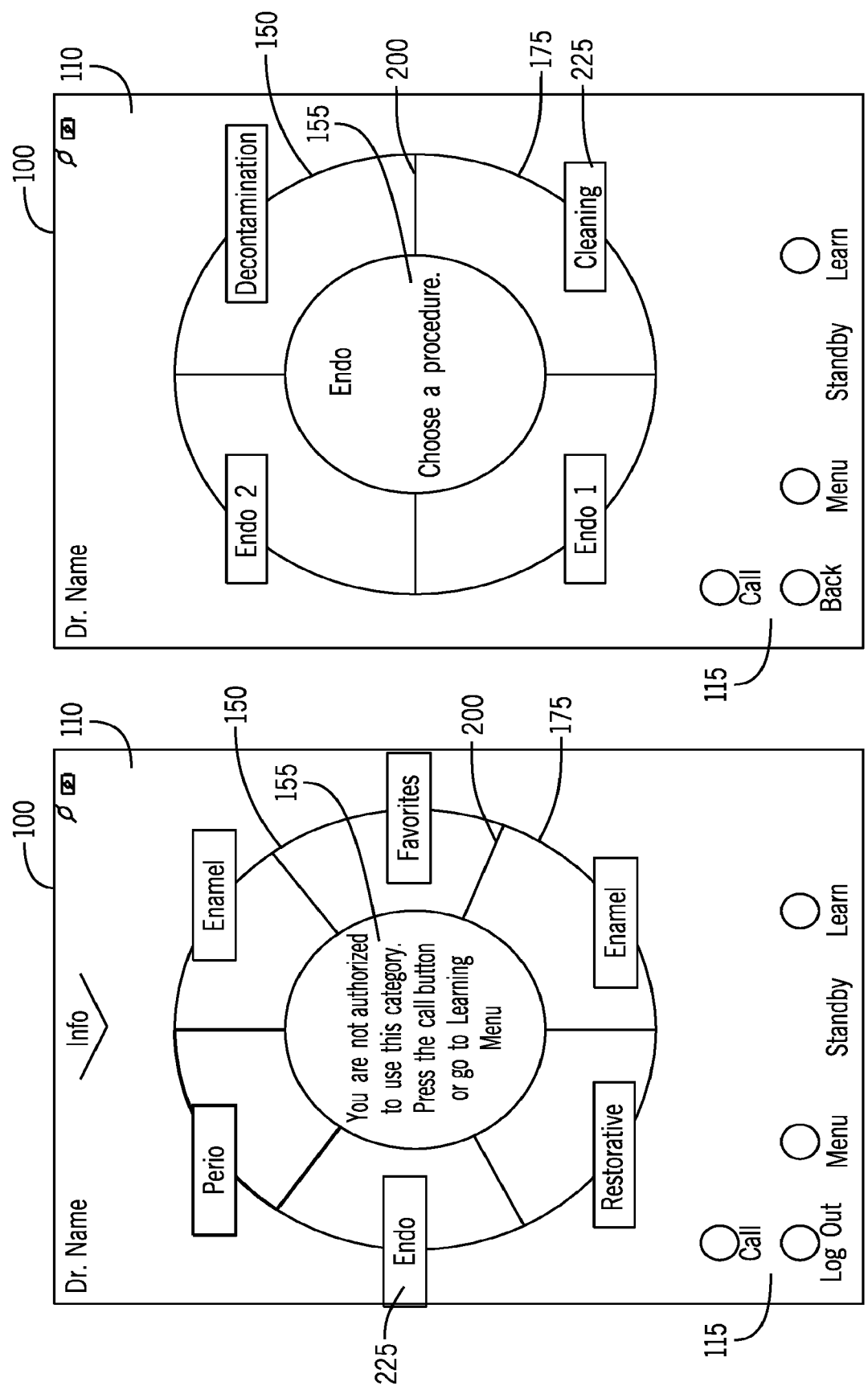

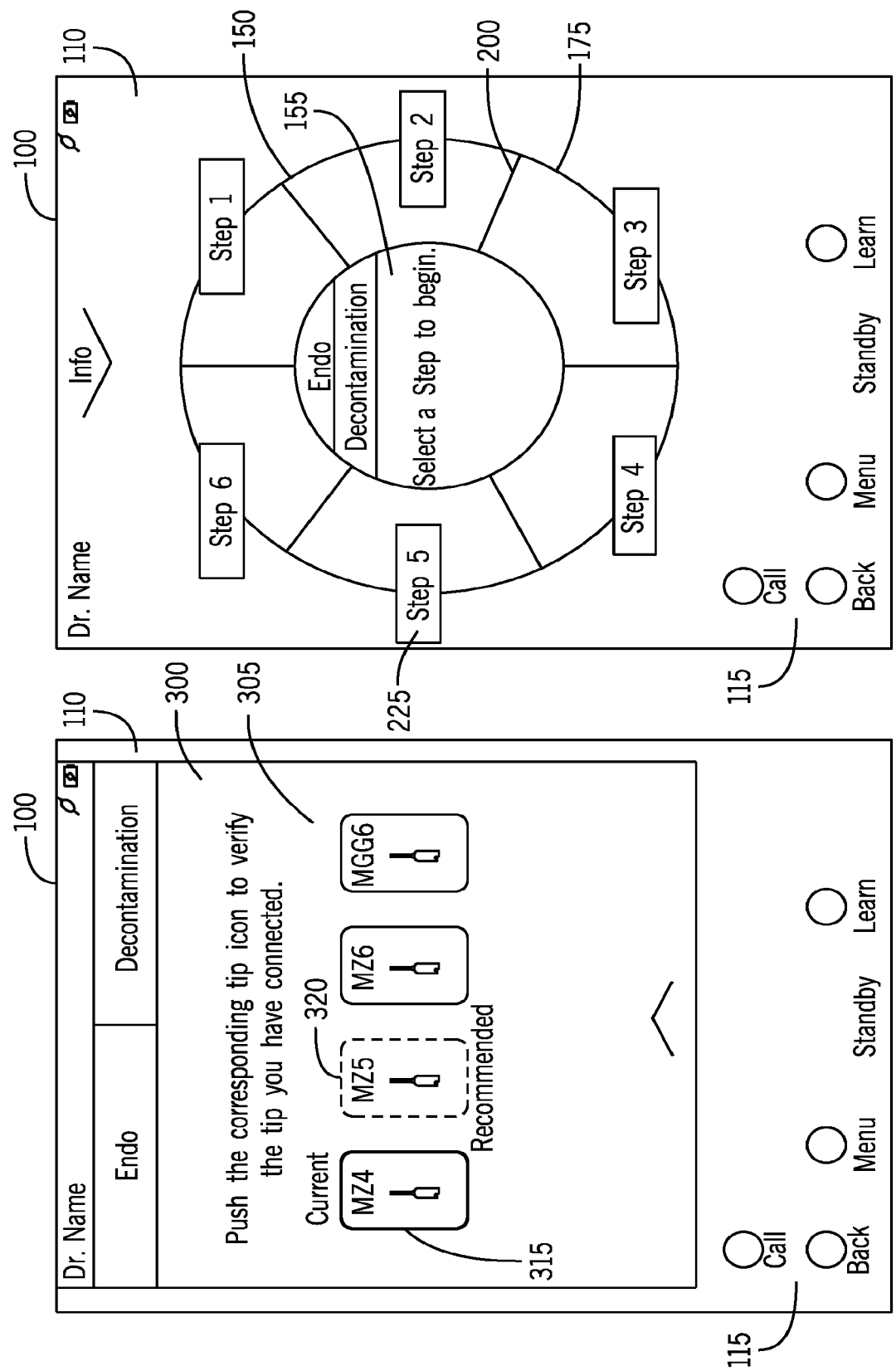

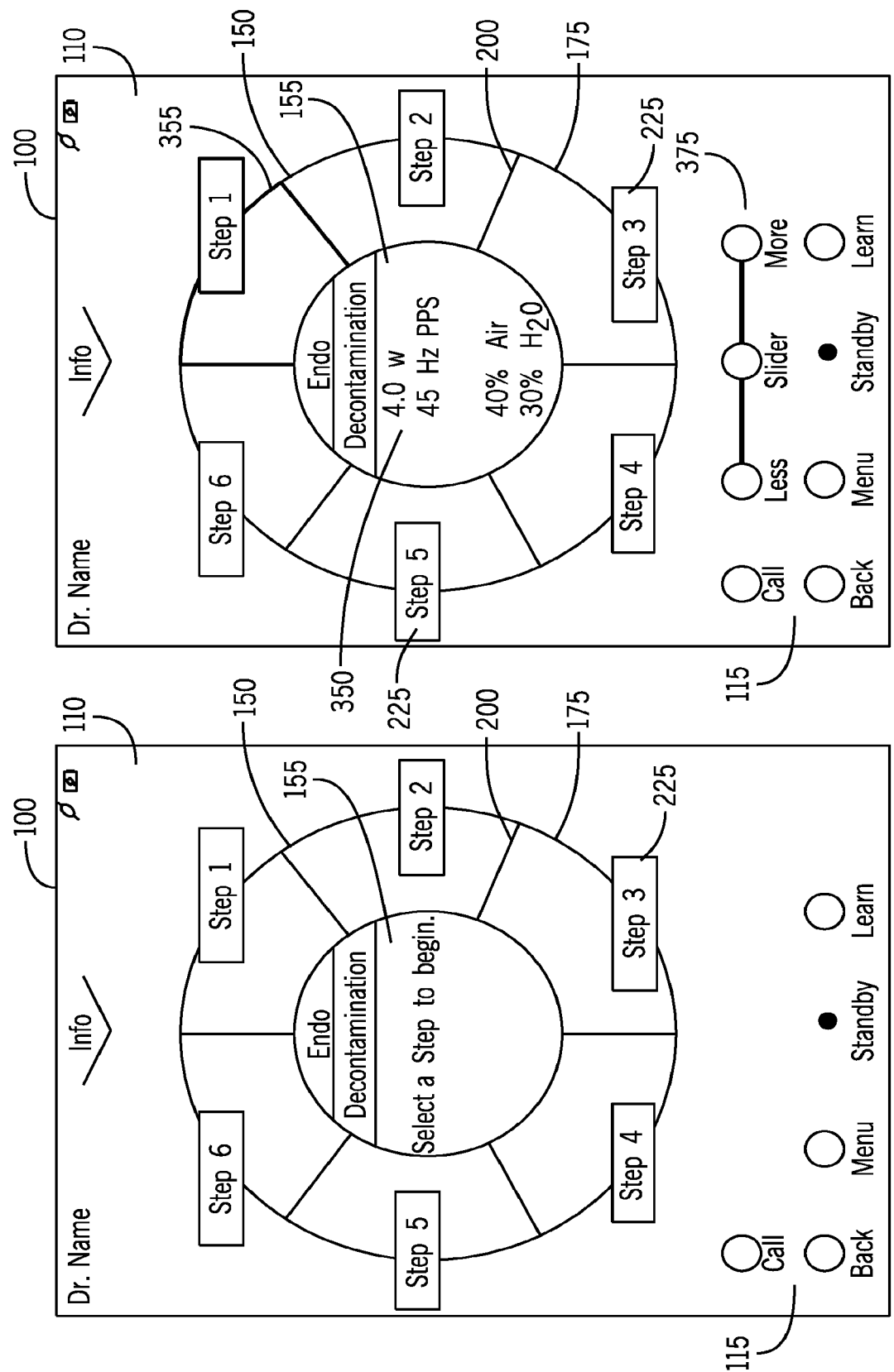

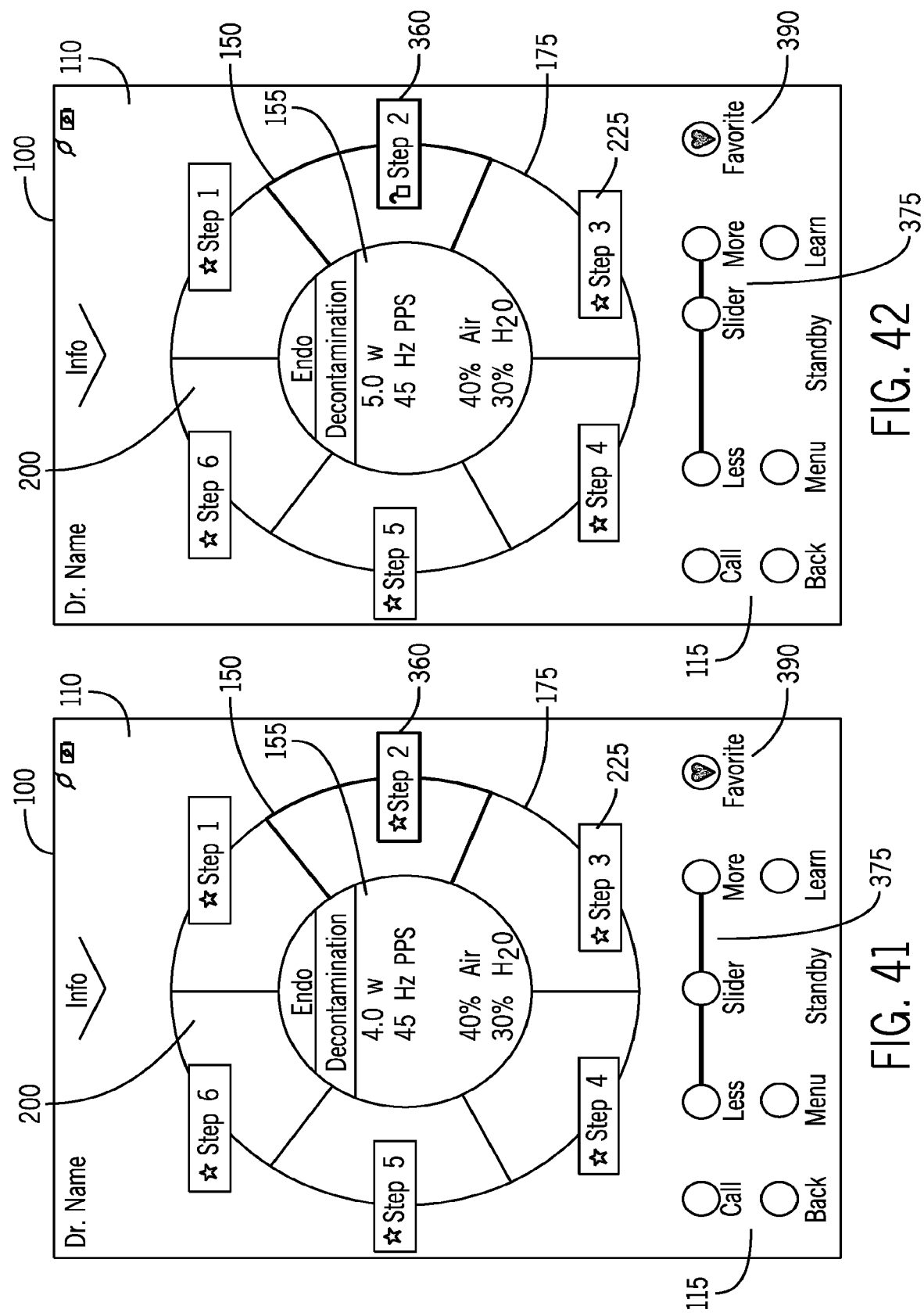

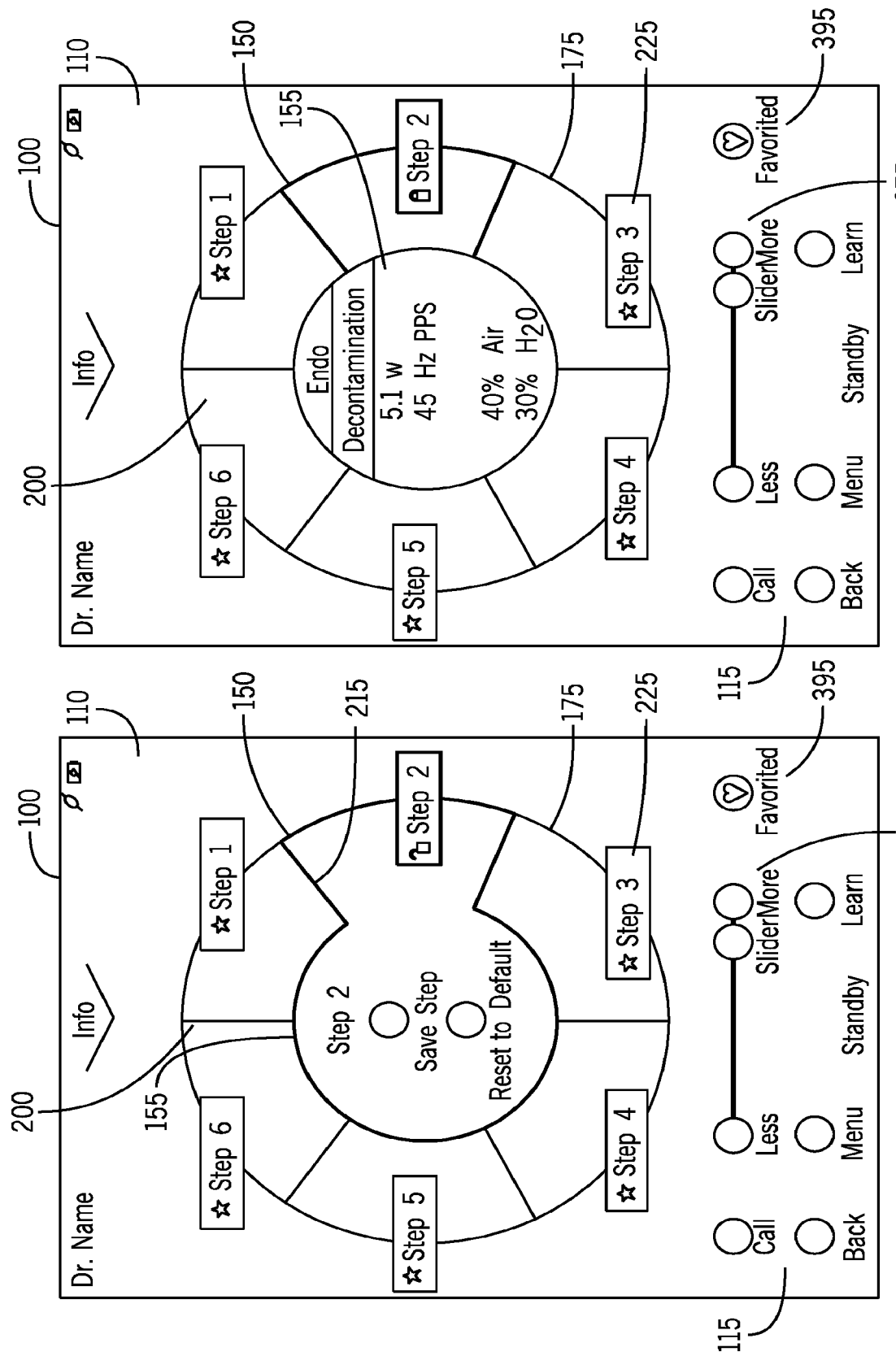

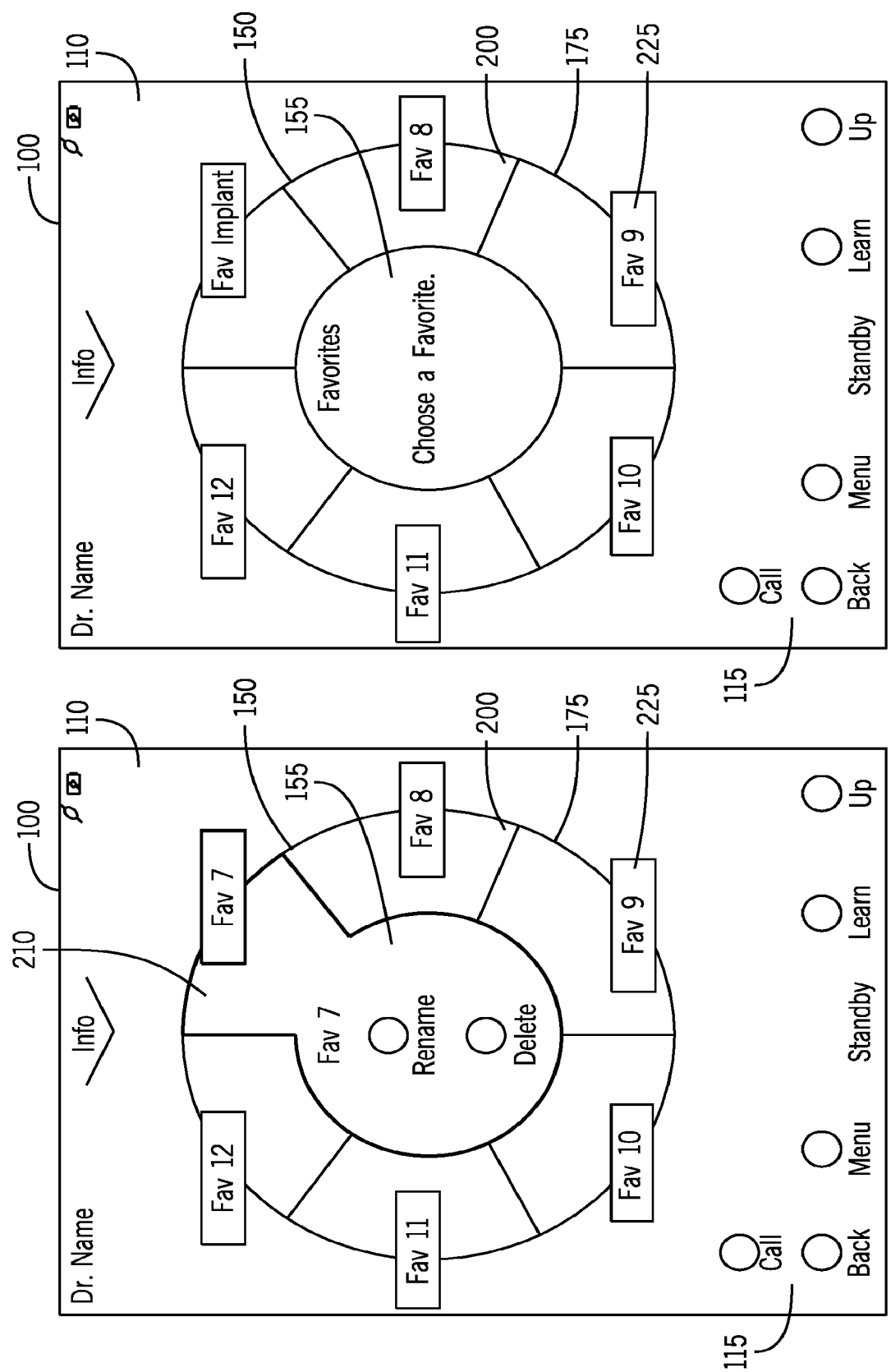

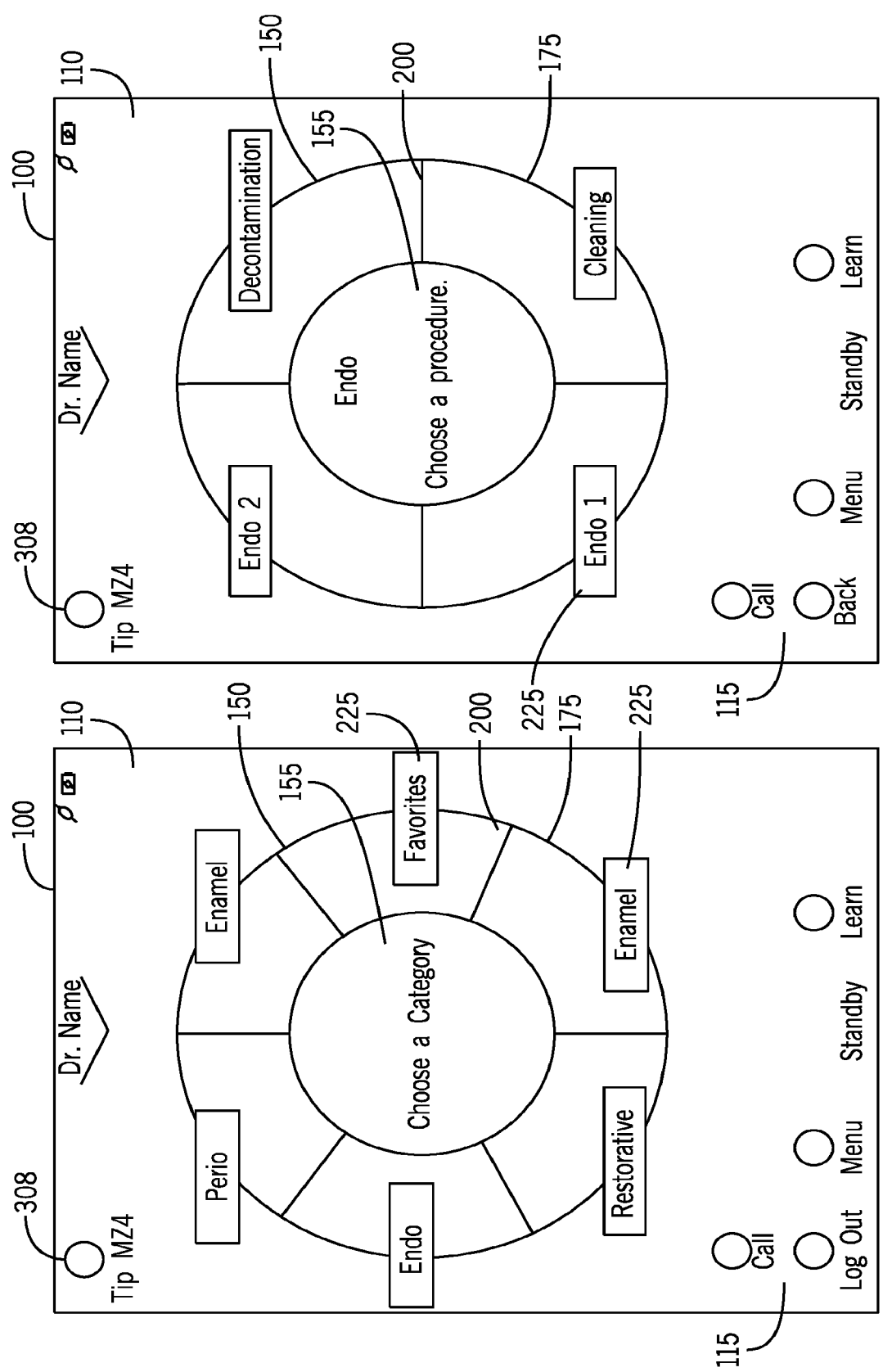

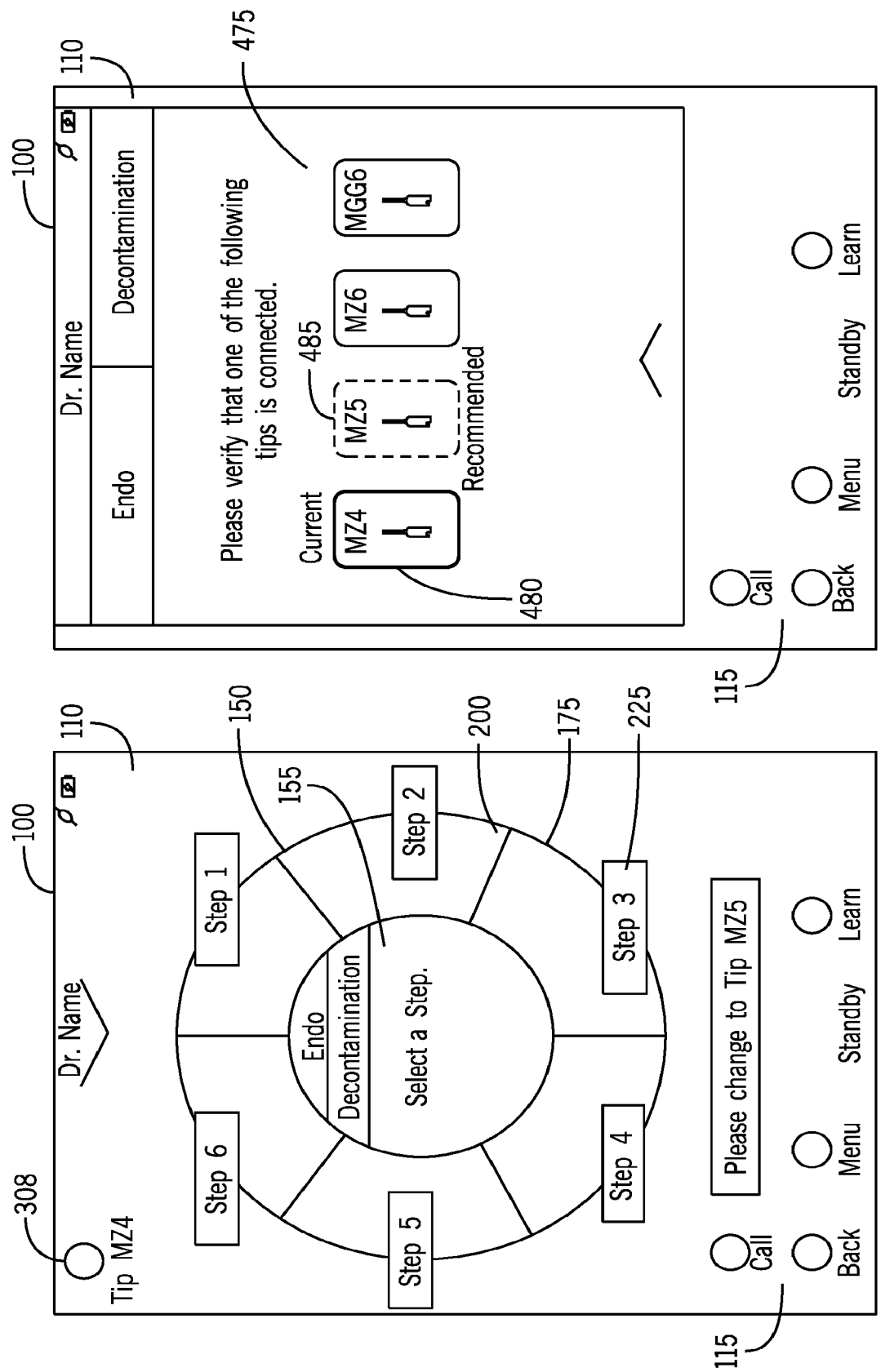

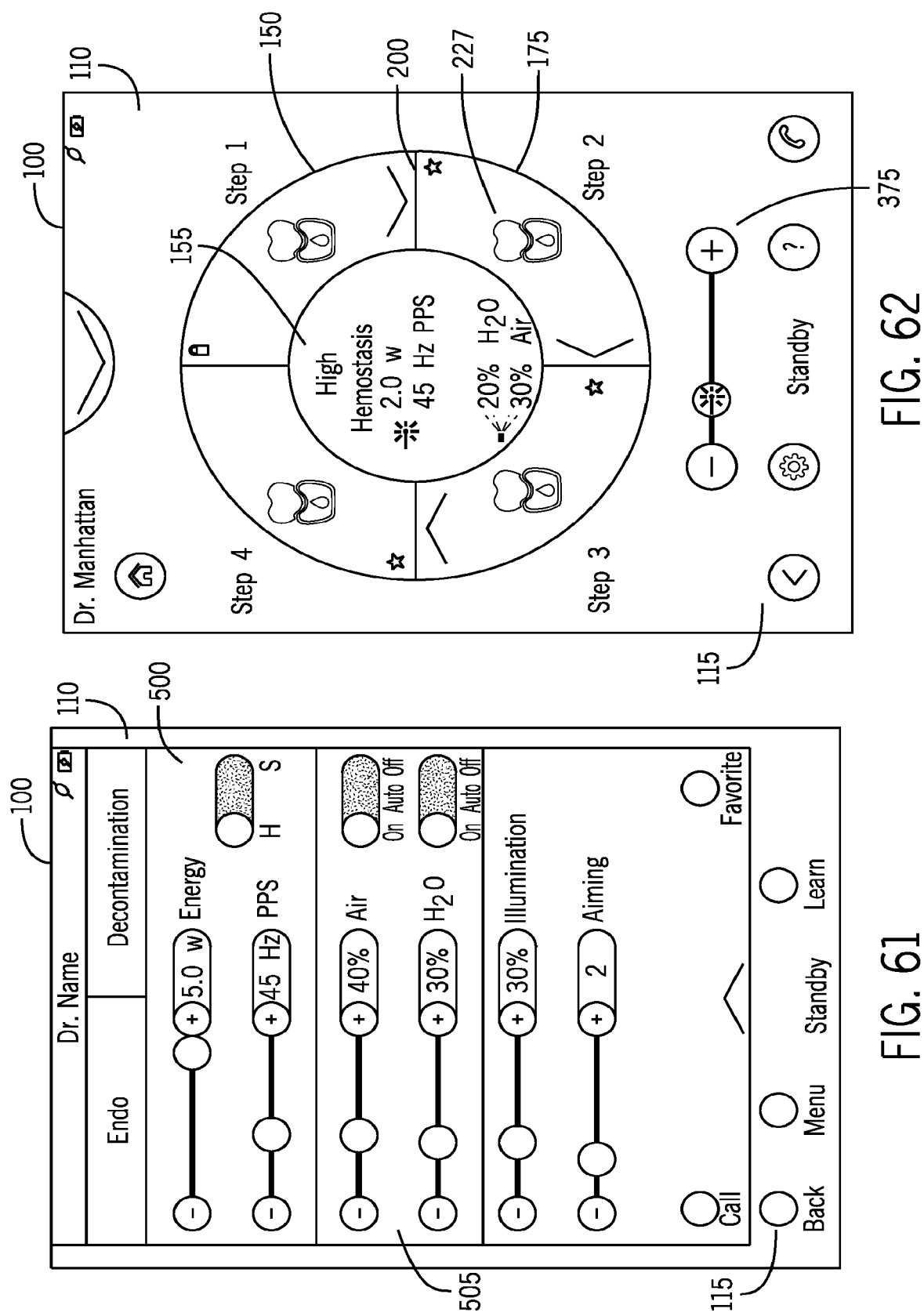

DENTAL LASER INTERFACE SYSTEM AND METHOD

RELATED APPLICATIONS

This application is a Continuation Application of U.S. patent application Ser. No. 17/104,590, filed Nov. 25, 2020, which is a Continuation Application of U.S. patent application Ser. No. 15/866,173, filed Jan. 9, 2018, which is a Continuation Application of U.S. patent application Ser. No. 14/666,287, filed Mar. 23, 2015, which claims priority from Provisional Application No. 61/968,632, filed Mar. 21, 2014, the entire contents of which are incorporated herein by reference.

BACKGROUND

The increasing range and sophistication of dental tools has broadened their appeal within the dental community. Nowadays, most dental practices will have at least one complex dental laser station that can include various control systems, displays, and one or more user interfaces of various forms that can be used to control the tool, and/or monitor and communicate some function or operational characteristic of the tool.

In most systems available on the market today, the user interface is often complex, and typically does not enable the dentist to choose or update the visual or operational characteristics of the interface. This can be especially limiting to specialized fields of dentistry. For example, most interfaces will appear and operate the same regardless of whether the practicing dentist is a dentist practicing as a general dentist, an oral surgeon, an orthodontist, etc. Of the tools that do enable some modification of the user interface, the procedures are often buried in various layers of the interface and require multiple inputs or updates.

SUMMARY

Some embodiments include a dental laser control system comprising at least one computer system including at least one processor that is configurable to control at least one function of a dental laser, and at least one user display including at least one graphical user interface configured and arranged to exchange information with the at least one controller. Some embodiments include a non-transitory computer-readable storage medium configured to tangibly store thereon program logic for execution by the at least one processor. In some embodiments, the program logic includes a dental laser control system that when executed by the at least one processor, is configured to update the at least one graphical user interface. In some embodiments, the update can include rendering a first display at least partially encircled by an second display, where the second display comprises at least one user-selectable segment, and rendering at least one menu navigation portion adjacent the at least one user-selectable segment. In some embodiments, the at least one menu navigation portion includes displayed information related to any user-actuable function represented by any one of the user-selectable segments. In some embodiments, following selection of a segment by a user through interaction with graphical user interface, the at least one processor is configured by the program logic to render the segment with a distinguishing graphical look, and to initiate a control sequence accessing or controlling one or more of the functions of the dental laser.

In some embodiments, after initiating the control sequence, the at least one processor is configured by the program logic to receive data from the dental laser indicative of a status or operation of the dental laser, and to provide an icon or graphical update within the at least one graphical user interface based at least in part on at least a portion of the received data.

In some embodiments, the second display extends the circumference of the first display. In some further embodiments, the second display includes at least one banner associated with a segment, where the at least one banner comprises a notification or description of a parameter or function represented by the segment.

In some embodiments, the menu navigation portion includes at least one section configured to provide information related to at least one sub-menu. In some further embodiments, the graphical user interface further comprises a display of a recommendation for one or more laser tips of the dental laser.

In some embodiments, the processor is further configured by the program logic to display a user-slidable slide bar and to provide input to the at least one controller based on user positioning of the slide bar. In some embodiments, the processor is further configured by the program logic to display associative icons that relate to dental categories, procedures, steps, or options. In some further embodiments, the processor is further configured by the program logic to display at least one video and graphics related to user a help guide.

In some embodiments, the second display comprises at least one of a user-selectable dental treatment category and user-selectable dental procedure. In some further embodiments, the second display comprises one or more selectable steps of a dental procedure represented as the at least one of the user-selectable segment. In some embodiments, the first display displays one or more parameters of any user-selected step of a dental procedure.

In some embodiments, the processor is further configured by the program logic to display a parameter display indicating one or more parameters of the dental laser station. In some embodiments, the program logic is configured to enable one or more of the parameters to be modified by the processor based on a user input to a slider bar displayed in the graphical user interface. In some further embodiments, the parameter display includes a display of laser power based at least in part on a user's operation of the slider bar.

In some embodiments, the second display comprises at least one user-defined or selected favorite dental procedures or favorite steps of a dental procedure represented as at least one of the at least one user-selectable segments. In some embodiments, the selection of the at least one user-selectable segment occurs based on a user's touch of the user display of a segment.

Some embodiments include a non-transitory storage medium comprising a non-transitory computer-readable storage medium configured to tangibly store thereon program logic for execution by at least one processor. The program logic includes a dental laser control system that when executed by the at least one processor, is configured to display or update at least one user interface by displaying at least a portion of a graphical user interface on at least one user display. In some embodiments, the at least one user display is configured and arranged to exchange information with at least one dental laser controller. In some embodiments, the program logic is configured to enable the processor to render a first display on the graphical user interface that is at least partially encircled by an second display comprising at least one user-selectable segment. In some embodiments, the program logic is configured to enable the processor to render on the graphical user interface at least one menu navigation portion adjacent the at least one user-selectable segment, where the menu navigation portion includes displayed information related to any user-actuable function represented by any one of the user-selectable segments. Further, in some embodiments, following selection of a segment by a user through interaction with graphical user interface, the at least one processor is configured by the program logic to render the segment with a distinguishing graphical look, and to initiate a control sequence accessing or controlling one or more of the functions of the dental laser.

In some embodiments, the processor is further configured by the program logic to display a user-slidable slide bar, and to provide input to the at least one controller based on user positioning of the slide bar. In some further embodiments, the processor is further configured by the program logic to display associative icons that relate to dental categories, procedures, steps, or options.

DESCRIPTION OF THE DRAWINGS

FIG. 3 illustrates a display with a user interface for controlling a dental laser station including example docking station guide icons in accordance with some embodiments of the invention.

FIG. 6 illustrates a display with a user interface for controlling a dental laser station displaying a control wheel in accordance with some embodiments of the invention.

FIG. 7 illustrates a display with a user interface for controlling a dental laser station displaying a control wheel in accordance with some embodiments of the invention.

FIG. 12 illustrates a display with a user interface for controlling a dental laser station showing a video and animations menu in accordance with some embodiments of the invention.

FIG. 13 illustrates a display with a user interface for controlling a dental laser station showing a video and animations menu in accordance with some embodiments of the invention.

FIG. 24 illustrates a display with a user interface for controlling a dental laser station displaying a control wheel in accordance with some embodiments of the invention.

FIG. 25 illustrates an icon legend of a display with a user interface for controlling a dental laser station in accordance with some embodiments of the invention.

FIG. 26 illustrates handpieces and tips selection menu of a display with a user interface for controlling a dental laser station in accordance with some embodiments of the invention.

FIG. 27 illustrates a key menu of a display with a user interface for controlling a dental laser station in accordance with some embodiments of the invention.

FIG. 28 illustrates an information menu of a display with a user interface for controlling a dental laser station in accordance with some embodiments of the invention.

FIG. 31 illustrates a display with a user interface for controlling a dental laser station displaying a control wheel in accordance with some embodiments of the invention.

FIG. 32 illustrates a display with a user interface for controlling a dental laser station displaying a control wheel in accordance with some embodiments of the invention.

FIG. 33 illustrates a display with a user interface for controlling a dental laser station displaying a tip selection menu in accordance with some embodiments of the invention.

FIGS. 34-47 illustrate displays with user interfaces for controlling a dental laser station displaying example procedure control wheel displays in accordance with some embodiments of the invention.

FIGS. 49-55 illustrate displays with user interfaces for controlling a dental laser station displaying example control wheels in accordance with some embodiments of the invention.

FIGS. 56-57 illustrate displays with user interfaces for controlling a dental laser station including an example tip check displays in accordance with some embodiments of the invention.

FIGS. 58-59 illustrate displays with user interfaces for controlling a dental laser station displaying example control wheels in accordance with some embodiments of the invention.

FIGS. 60-61 illustrate displays with user interfaces for controlling a dental laser station including control parameter selection tools in accordance with some embodiments of the invention.

FIG. 62 illustrates a display with a user interface for controlling a dental laser station display an example control wheel in accordance with some other embodiments of the invention.

DETAILED DESCRIPTION

Figure 1:
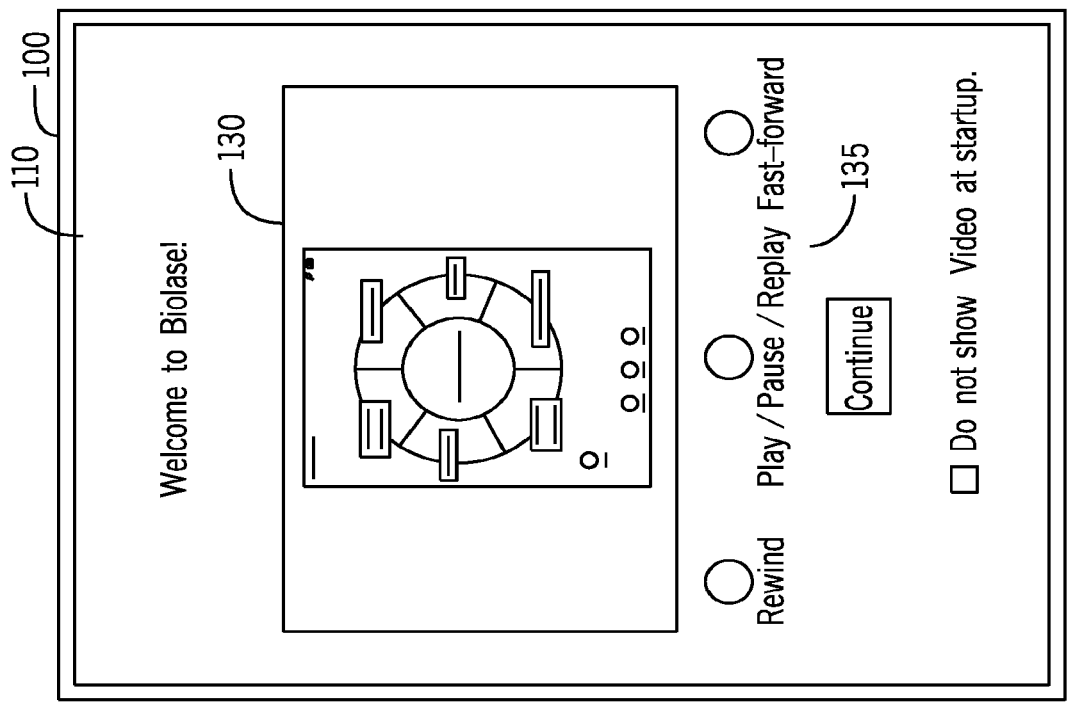
FIG. 1 illustrates a display with a user interface in an example start-up mode in accordance with some embodiments of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives that fall within the scope of embodiments of the invention.

The various embodiments of the invention described herein include systems and methods to enable the control and/or monitoring of complex dental laser stations using interfaces that can be customized or easily changed using a single control. Embodiments of the invention include control systems, displays, and associated user interfaces that can be used to control some aspect of a dental laser station, and/or communicate some function or operational characteristic of the tool to the user. For example, the invention can include control systems, displays, and user interfaces that can be used to control dental laser stations or related dental restorative and oral disease prevention tools. More specifically, the various embodiments of the invention described herein include systems and methods to enable the operate and/or monitor the functional aspects of dental laser stations using interfaces that can be customized for a specific dental procedure and/or for any specific dental specialty including, but not limited to general dentistry, oral and maxillofacial dentistry, orthodontic dentistry, endodontic dentistry, pediatric dentistry, cosmetic dentistry, and so on.

Embodiments of the invention can include a graphical user interface (hereafter "GUI") that comprises a menu that is organized based upon a one or more GUI category buttons, any one of which can have one or more control system attributes. These category buttons may be defined as but not limited to: dentin, enamel, anterior deciduous, hemostasis, perio, endo, incision/excision, desensitation and osseus. The buttons may be "soft" buttons in the GUI (i.e., graphically displayed buttons), hard buttons adjacent on the machine, and/or a remote control or WiFi linked system. The attributes can be singularly controlled and/or controlled in control system in two or more groupings. This control may take the form but not limited to a knob metaphor of a category button that can control one or more attribute systems. For example, the knob metaphor may be turned left for less power, slower speed, less percentage, etc., or for more power, faster speed, higher percentage, etc. This can enable the control of up to twelve or more attribute systems such as not limited to: Air-%, Power-watts, Pulse-ms, H20%, illumination %, aiming beam %, diode power-w, YSGG power. These relationships can increase/decrease, can be changed, modified interactively, or singularly/interactively based upon waveform systems to optimize the dental procedures. The menu may be in the form of a circular pie chart or in the form of at least one standard drop down menu. This system may be used with a laser system or in combination with other systems. Further, a procedure set up menu can allow a user to interactively modify the menu, including, for example, to add or subtract category buttons, to modify attribute values, and/or to allow personification of a specific doctor's preference system.

Throughout the description and the FIGS. 1-62 described below, the display can comprise "soft" buttons that are graphically rendered in a GUI, and/or hard buttons adjacent on a dental tool or control equipment, and/or a remote control or a WiFi linked system. Further, the user interface can be graphically rendered in a display or can form part of the display (i.e. a GUI), and/or can be a user interface embodied in the physical hardware of a dental tool or control equipment, and/or a remote control or WiFi linked system. Embodiments of the invention that include a GUI can include at least one GUI that is rendered on and/or is contained within a touchscreen display. For example, in some embodiments, the display can comprise a touchscreen display that is configured to enable a user to interact with the displayed GUI using a single, multiple or repeated physical contact with the display. Further, in some embodiments, user actions with the GUI can include contact of at least a portion of the display to represent an input to the display and/or input or selection of any information within the display or GUI.

FIG. 1 illustrates a display 100 with a user interface 110 in an example start-up mode in accordance with some embodiments of the invention. The user interface 110 can be graphically rendered in the display 100 or form part of the display 100 that can be coupled to or integrated with a computing system and/or controller that is booted from a cold status (e.g., as a first time start up). In some embodiments of the invention, the display 100 including user interface 110 can be housed within or be coupled to one or more control and/or monitoring tools that can be configured to interface with one or more dental laser stations. For example, in some embodiments, the display 100 including user interface 110 can be housed within the dental laser station or be coupled to a docking station 20 that can interface with a dental laser station 10 (e.g., see docking station 20 coupled to a dental laser station 10 shown in FIG. 3). In some embodiments, the dental laser station 10 can comprise a dental laser. In other embodiments, the dental laser station 10 can comprise any dentistry equipment including or not including a laser. Some other embodiments of the user interface 110 can be used for a wide variety of laser equipment.

In some embodiments, during or following start-up, the user interface 110 can include one or more alerts, status updates, and/or check status prompts. In some embodiments, the one or more alerts, status updates, and/or check status prompts can include a check of the completeness of a specific configuration related to the dental laser station 10, docking station 20, display 100, or combinations thereof. In some embodiments, a user can tap on the display 100 to wake display from hibernation or suspension. The screen can provide a system status such as an updated legend or animation to show the progress of the wake-up and/or an intro display 120. In some embodiments, the user interface 110 can include one or messages and/or icons of function such as function icons 115, and/or status icons 125. For example, in some embodiments, the user interface 110 can display status icons 125 that can be configured to display information and/or provide a status update or alert regarding one or more functional, operational parameters related to the display 100 and/or the dental laser station 10 and/or the docking station 20. For example, in some embodiments, the status icons 125 can comprise a status icon 125*a*, and/or status icon 125*b*, and/or status icon 125*c*, and/or status icon 125*d*. In some embodiments, the status icon 125*a* can be updated with a warning dialog if the docking station 20 is not docked. In some embodiments, the status icon 125*b* can be updated with a warning dialog if the dental laser station and/or the docking station 20 are unplugged. Further, in some embodiments, the status icon 125*c* can be updated with a warning dialog if the breaker is not on. Further, in some embodiments, the status icon 125*d* can be updated with a warning dialog if the key is not in the on position.

Figure 2:
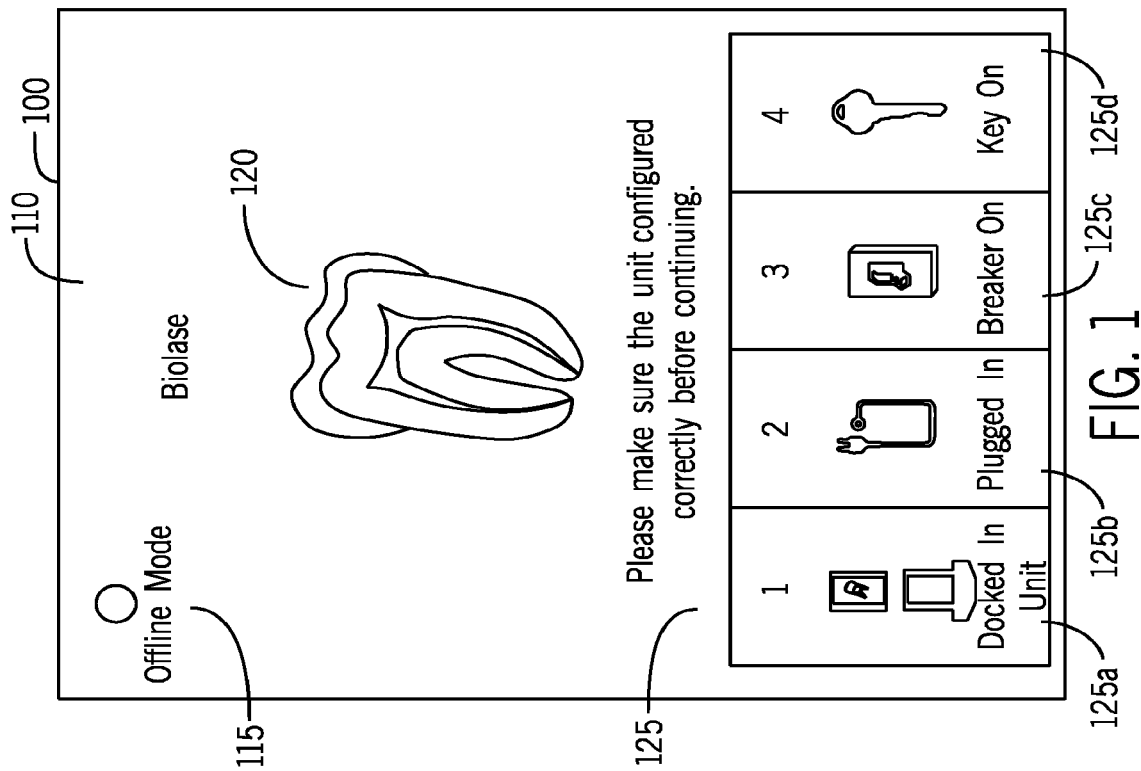
FIG. 2 illustrates a display with a user interface for controlling a dental laser station with video tutorial options in accordance with some embodiments of the invention.

Referring to FIG. 2, illustrating a display 100 with a user interface 110 for controlling a dental laser station 10, in some embodiments, following start-up and the various system checks and notifications described above with respect to FIG. 2, the viewing user can be presented with video tutorial options to assist in various operational aspects of the system (i.e., the docking station 20 coupled to the dental laser station 10). For example, in embodiments, the user interface 110 can include a video display 130 and associated video controls 135 that can be displayed during a first-time start up and/or when a new software update has occurred. In some embodiments, the video display 130 can reset after first start up, which can be controlled by leaving unchecked a choice indicator defining whether a video should be shown at start up or not (displayed in the user interface 110). Using the video controls 135, a user can view a system tutorial video, and then proceed to enter a product license registration after a prompt on the display 100.

FIG. 3 illustrates a display 100 with a user interface 110 for controlling a dental laser station 10 including example embodiments of docking station guide labels or icons. As described earlier, the dental laser station 10 can include a coupled docking station 20. A mobile interface 25 including the display 100 can be coupled to the dental laser station 10 using the docking station 20. For example, in some embodiments, the mobile interface 25 can comprise a mobile controller and/or computing device such as a tablet or a laptop computer that can be coupled to the docking station 20. In other embodiments, the mobile interface 25 can comprise a smart phone or other mobile display device that can be coupled to the docking station 20. In some embodiments, access, control and status icons 140 can be included with the dental laser station 10, docking station 20, and/or mobile interface 25. For example, in some embodiments, the access, control and status icons 140 can be physically coupled to the dental laser station 10, docking station 20, and/or mobile interface 25. In other embodiments, the access, control and status icons 140 can be rendered on the display 100.

Figure 5:
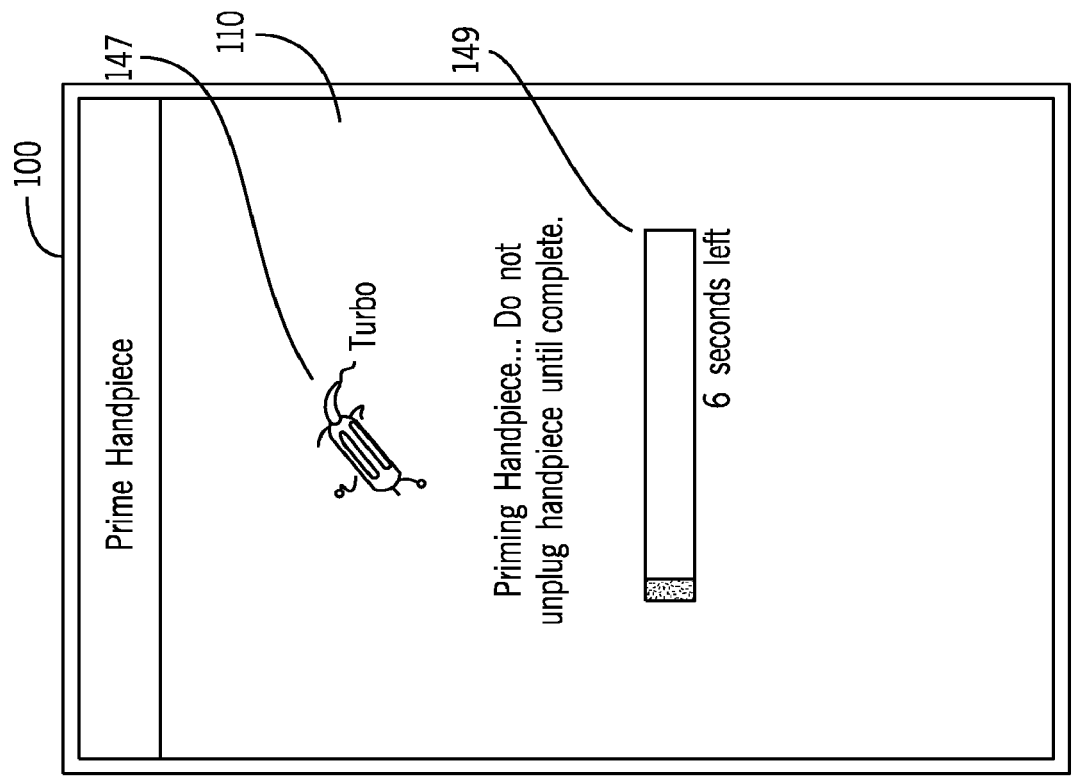
FIG. 5 illustrates a display with a user interface for controlling a dental laser station including a priming status in accordance with some embodiments of the invention.
Figure 4:
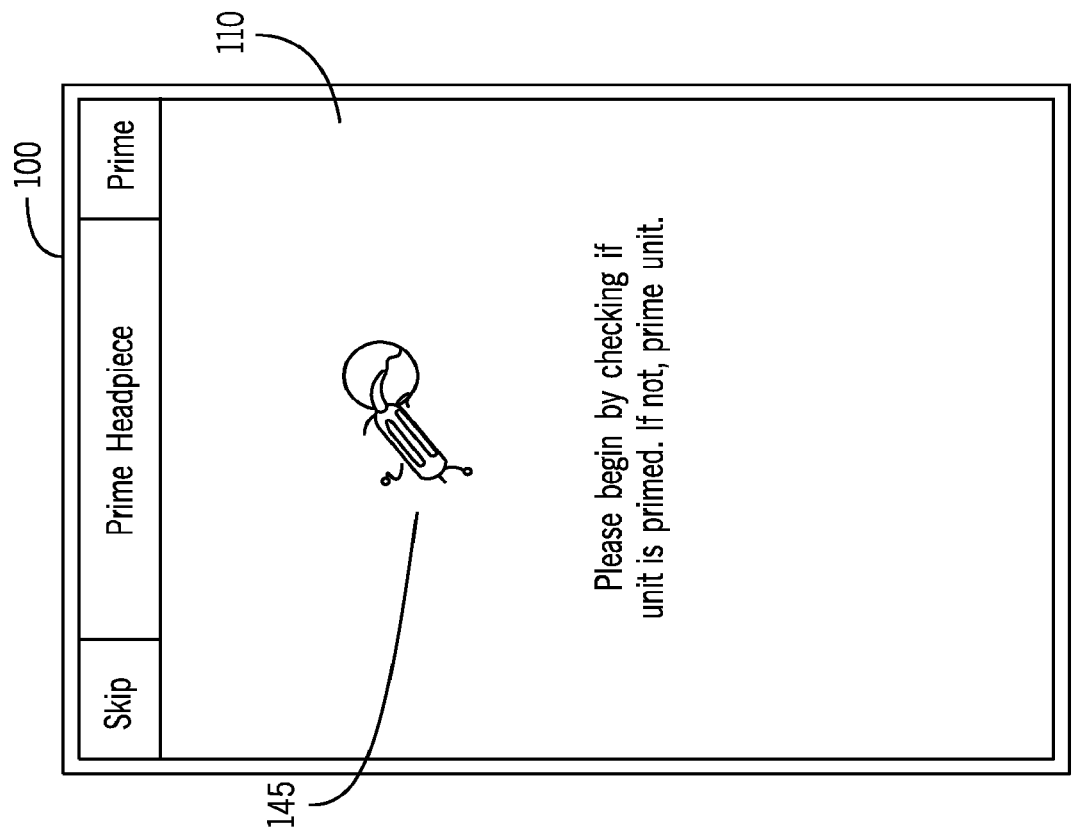
FIG. 4 illustrates a display with a user interface for controlling a dental laser station including a priming check screen in accordance with some embodiments of the invention.

FIG. 4 illustrates a display 100 with a user interface 110 for controlling a dental laser station 10 including a priming check screen in accordance with some embodiments of the invention. In some embodiments, the tool icon 145 can be displayed to enable a user to interact with the tool icon 145 to confirm a priming check of a coupled handpiece. In some embodiments, with a plurality of users using the dental laser station 10, an account selection page can be displayed prior to the priming check screen of FIG. 4. FIG. 5 illustrates a display 100 with a user interface 110 for controlling a dental laser station 10 including a priming status in accordance with some embodiments of the invention. In some embodiments, following an initiation of the priming of the handpiece, tool icon 147 can be displayed confirming a tool and tip priming with a status bar 149.

FIG. 6 illustrates a display 100 with a user interface 110 for controlling a dental laser station 10 displaying a control wheel 150 in accordance with some embodiments of the invention. In some embodiments, the control wheel 150 can be used to control and communicate one or more functions of the dental laser station 10.

Some embodiments include various function icons 115 that can be configured to navigate the display 100 and/or control one or more functions of the user interface 110. In some embodiments, the control wheel 150 can include a first display 155 at least partially surrounded by an second display 175. In some embodiments, the first display 155 can display information related to the function of the dental laser station 10. Further, in some embodiments, the first display 155 can include at least one user interaction element. In some embodiments, the second display 175 can be formed from segments 200. In some embodiments, the segments 200 can comprise a single segment. In other embodiments, the segments 200 can comprise multiple segments.

Figure 9:
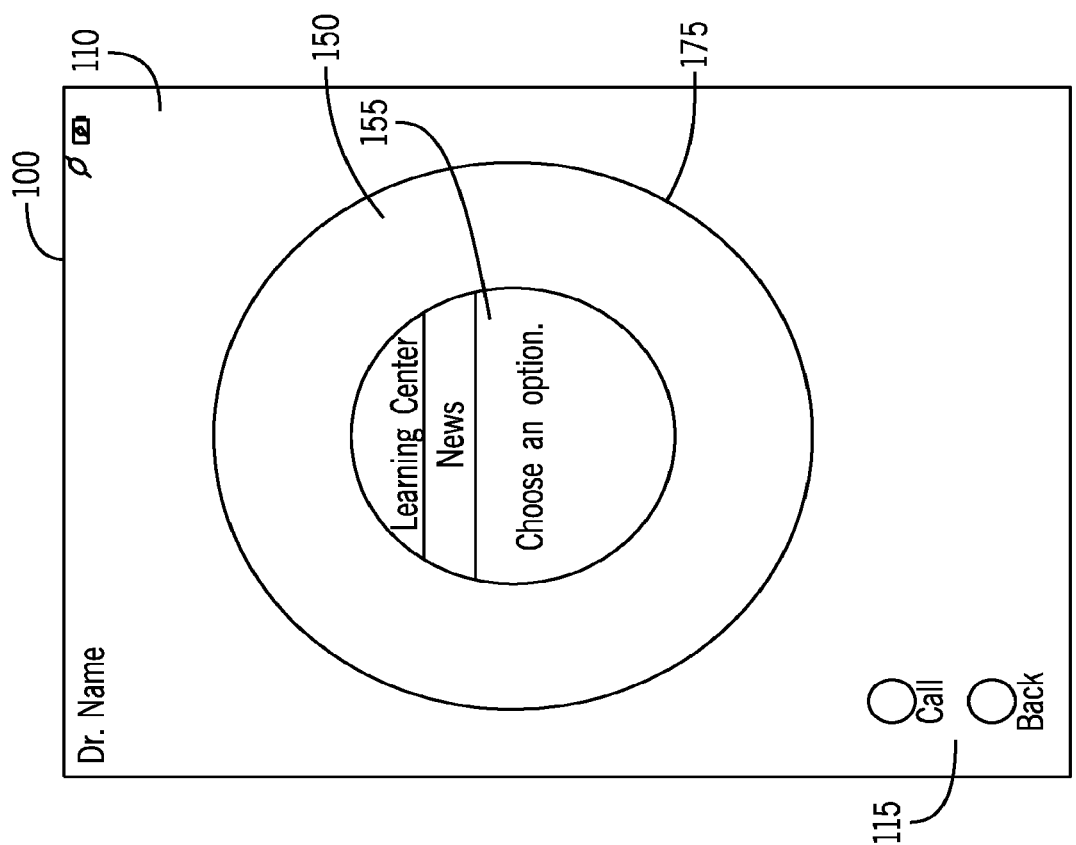
FIG. 9 illustrates a display with a user interface for controlling a dental laser station displaying a control wheel in accordance with some embodiments of the invention.
Figure 8:
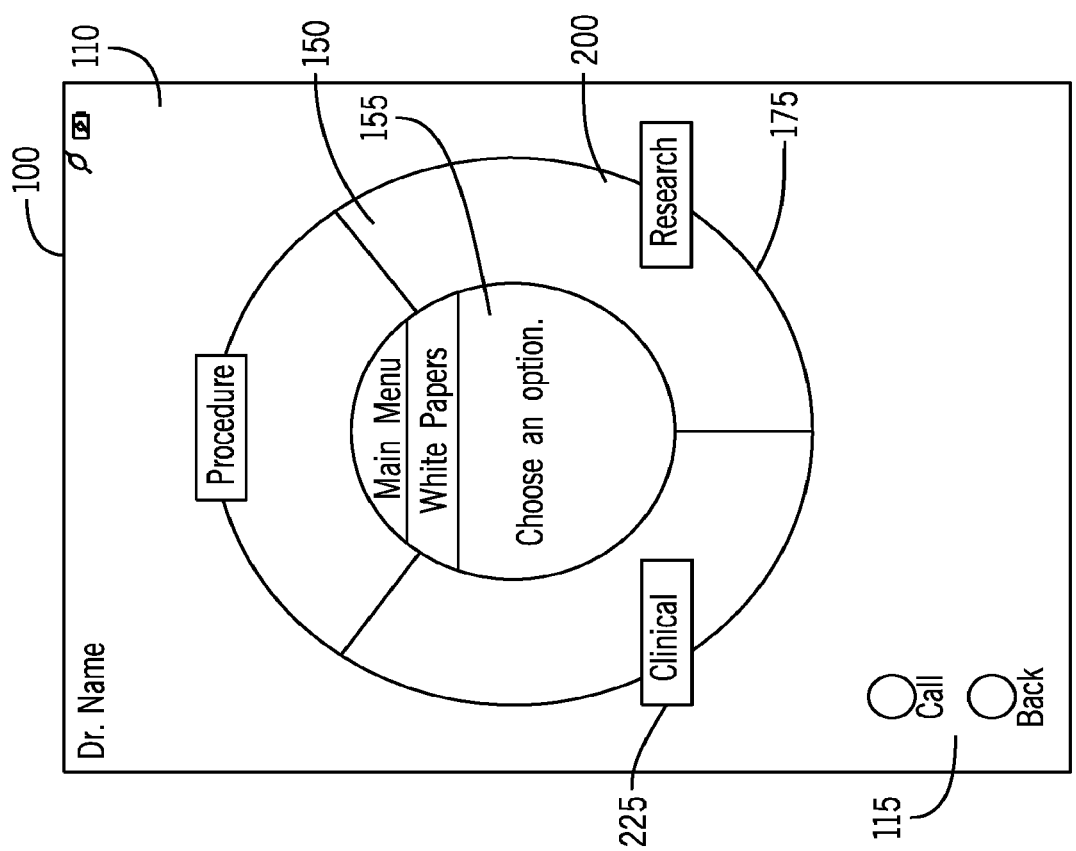
FIG. 8 illustrates a display with a user interface for controlling a dental laser station displaying a control wheel in accordance with some embodiments of the invention.

In some embodiments, any one of the segments 200 can be actuatable by a user. For example, in some embodiments, any one of the segments 200 can be selected by a user through a user interaction with the display 100. In some embodiments, any of the segments 200 can include banner content 225. In some embodiments, the banner content 225 can comprise a notification or description of the underlying segment 200. Further, in some embodiments, following a user selection of a specific segment 200, the contents of a variation of the contents of the specific banner content 225 of the chose segment 200 can be displayed in the first display 155, and the banner content 225 can be updated based on the selected content. For example, FIG. 7 illustrates a display 100 with a user interface 110 for controlling a dental laser station 10 displaying a control wheel 150 illustrating an example where a user selection of a "learning center" segment 200 can cause the control wheel 150 to update to banner content 225 related to "learning center". Further example embodiments of various menu and items selections from the "learning center" can be seen in FIGS. 8-11. For example, FIG. 8 illustrates a display 100 with a user interface 110 for controlling a dental laser station 10 displaying a control wheel 150 in accordance with some embodiments of the invention following a selection of "white papers" in the example of FIG. 7, and FIG. 9 illustrates a display 100 with a user interface 110 for controlling a dental laser station 10 displaying a control wheel 150 in accordance with some embodiments of the invention following a selection of "news" in the example of FIG. 7.

Figure 11:
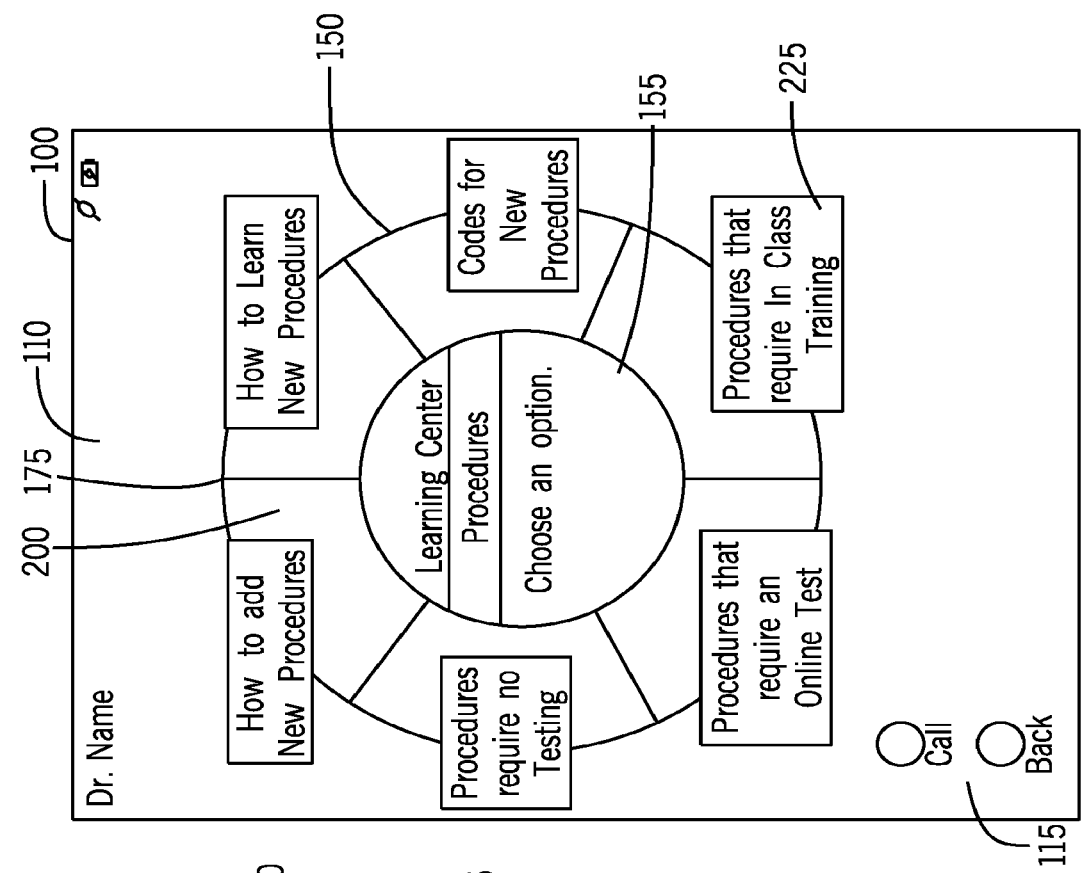
FIG. 11 illustrates a display with a user interface for controlling a dental laser station displaying a control wheel in accordance with some embodiments of the invention.
Figure 10:
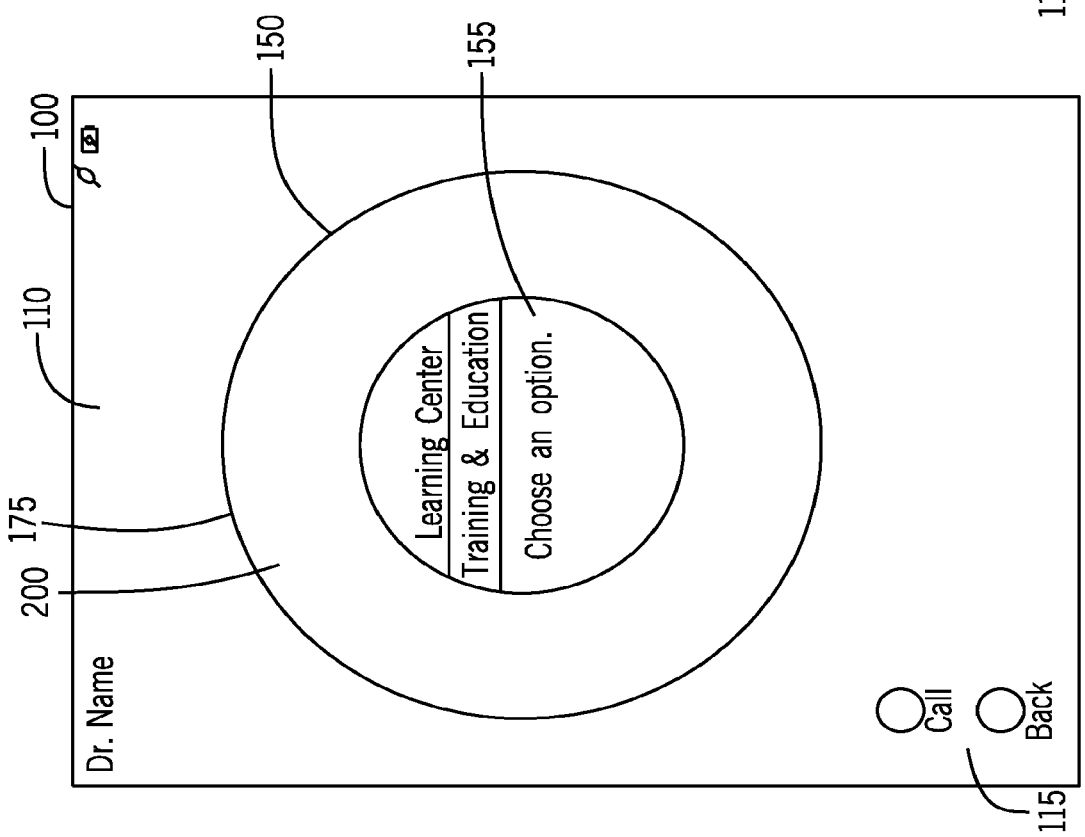
FIG. 10 illustrates a display with a user interface for controlling a dental laser station displaying a control wheel in accordance with some embodiments of the invention.

Further, FIG. 10 illustrates a display 100 with a user interface 110 for controlling a dental laser station 10 displaying a control wheel 150 in accordance with some embodiments of the invention following a selection of "training and education" in the example of FIG. 7. FIG. 11 illustrates a display 100 with a user interface 110 for controlling a dental laser station 10 displaying a control wheel 150 in accordance with some embodiments of the invention following a selection of "procedures" in the example of FIG. 7.

In some embodiments of the invention, videos and animations can be selected by the user for training and use guidance. For example, FIG. 12 illustrates a display 100 with a user interface 110 for controlling a dental laser station 10 showing a video and animations menu (video menu 160) in accordance with some embodiments of the invention. In some embodiments, the display 100 illustrated in FIG. 12 can be reached by a user following a selection of "Videos and Animations" in the example of FIG. 7. Referring to FIG. 13, illustrating a display 100 with a user interface 110 for controlling a dental laser station 10 showing a video and animations menu (menu 160), in embodiments of the invention, using the video menu 160, a user can select one or more videos or animations, for example, by selecting a videos icon 165.

Figure 15:
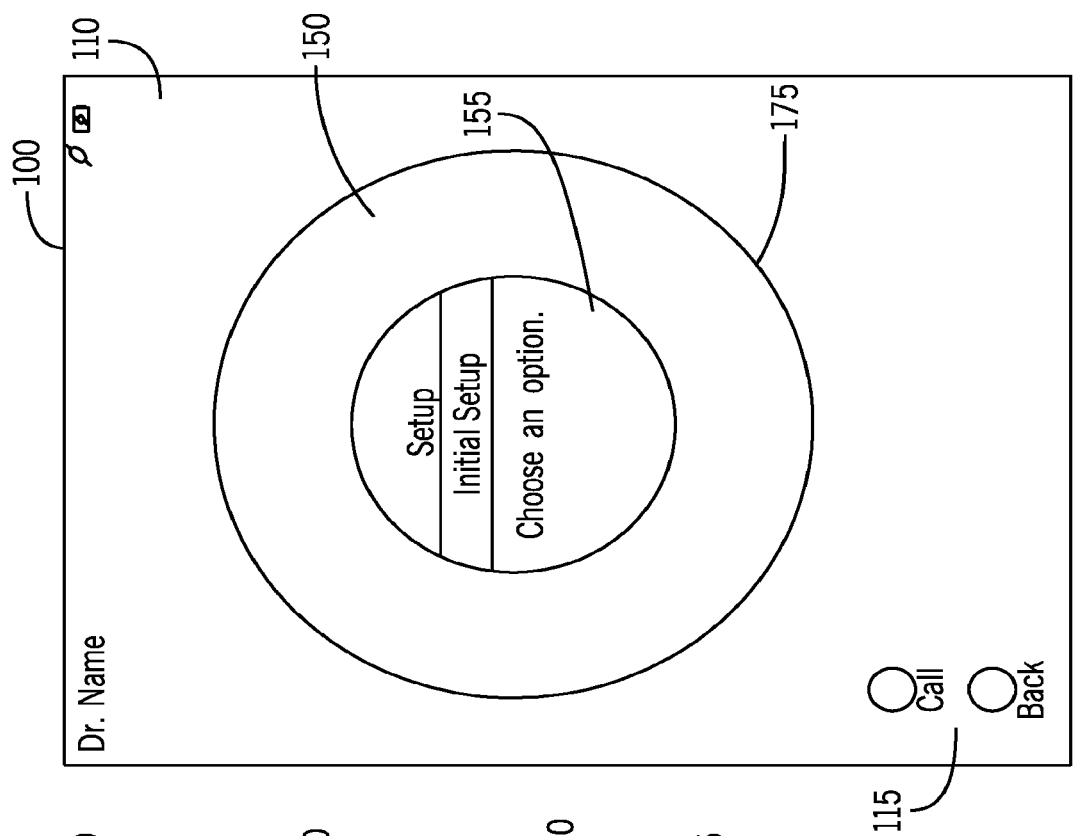
FIG. 15 illustrates a display with a user interface for controlling a dental laser station displaying a control wheel in accordance with some embodiments of the invention.
Figure 14:
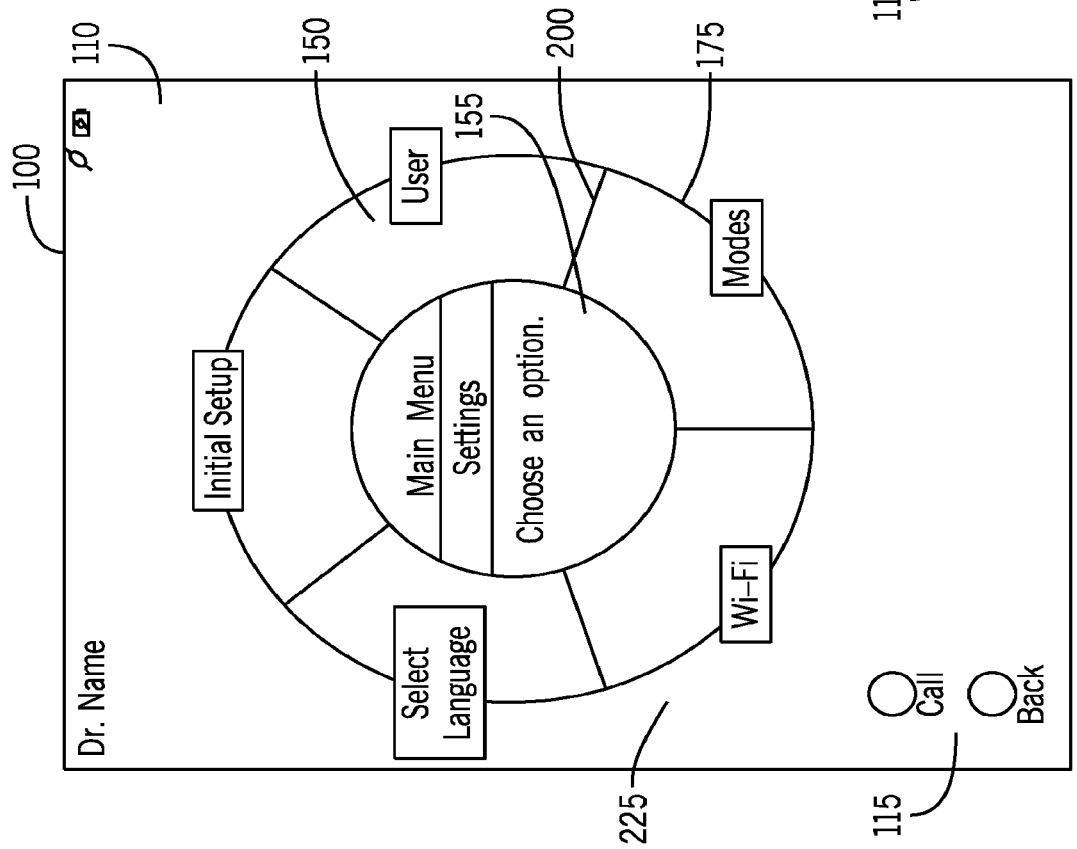
FIG. 14 illustrates a display with a user interface for controlling a dental laser station displaying a control wheel in accordance with some embodiments of the invention.
Figure 17:
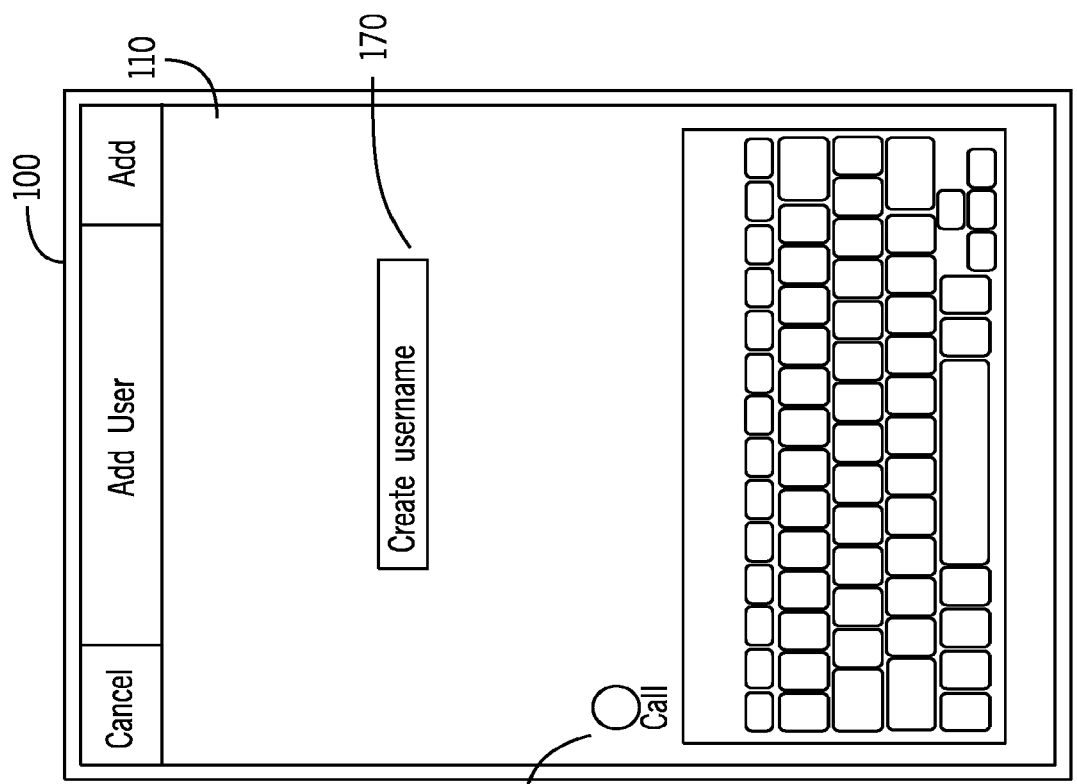
FIG. 17 illustrates a display with a user interface for controlling a dental laser station displaying an entry screen in accordance with some embodiments of the invention.
Figure 16:
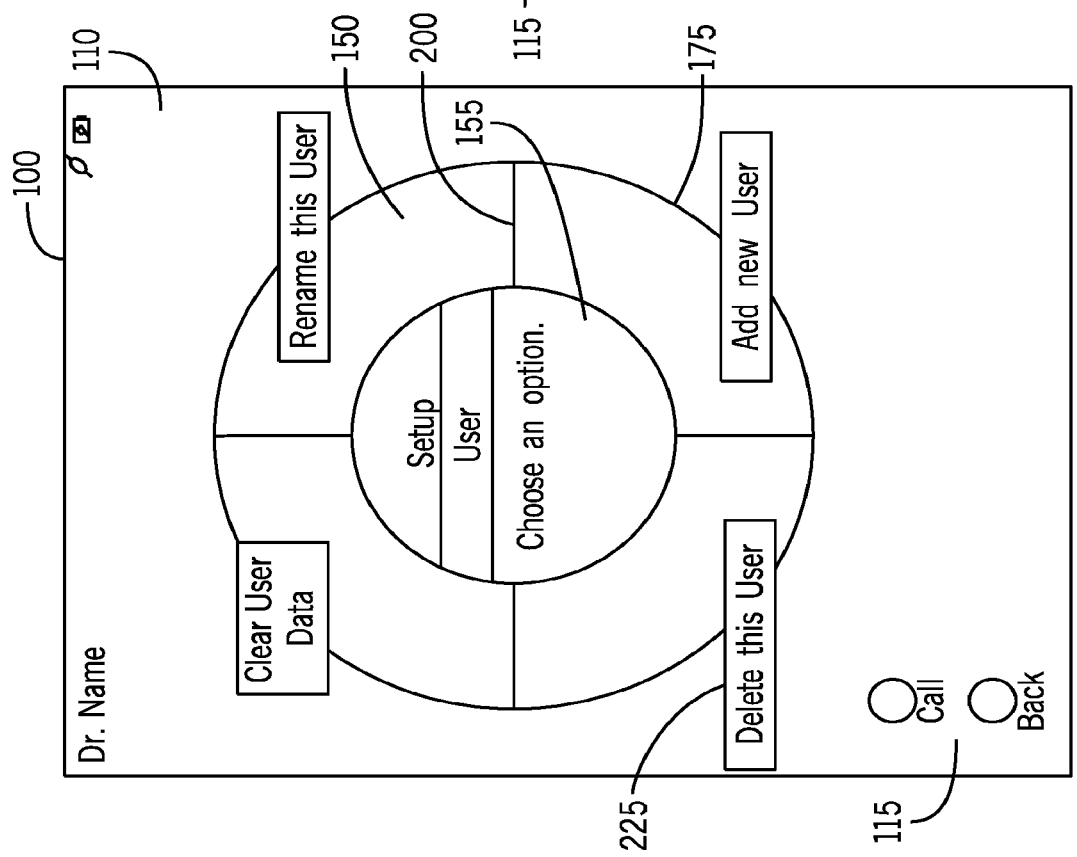
FIG. 16 illustrates a display with a user interface for controlling a dental laser station displaying a control wheel in accordance with some embodiments of the invention.
Figure 19:
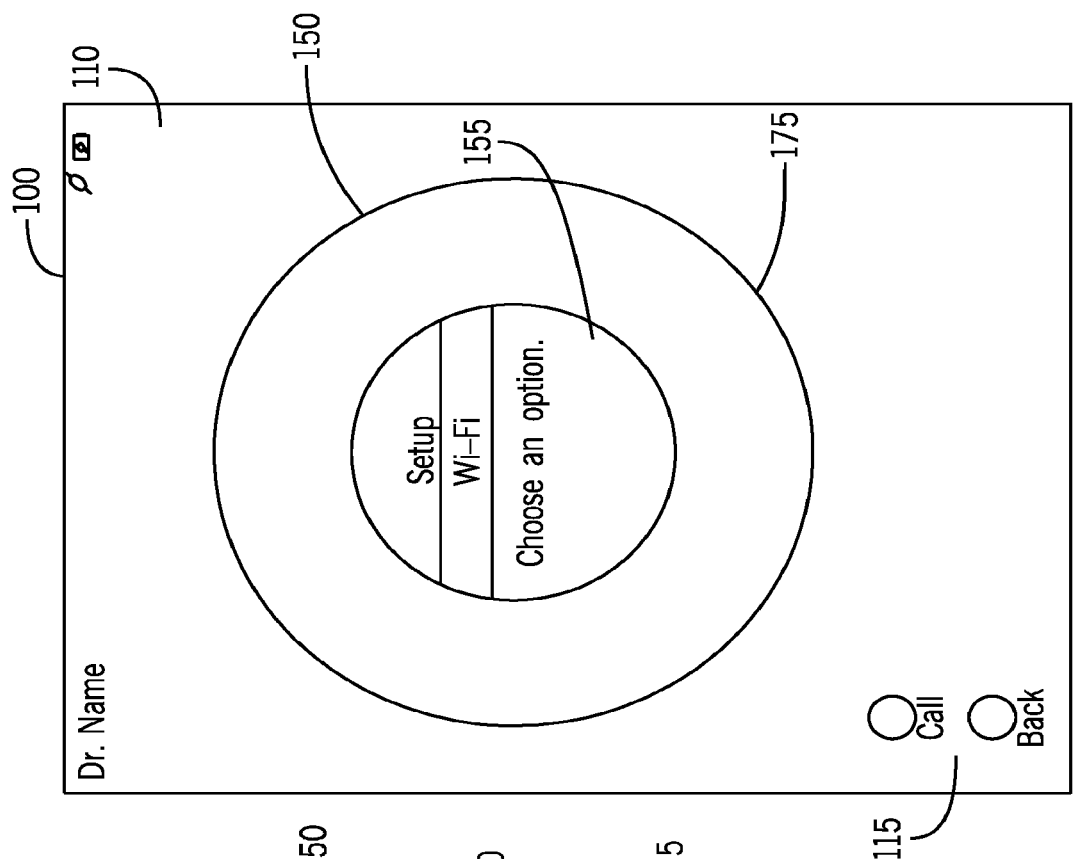
FIG. 19 illustrates a display with a user interface for controlling a dental laser station displaying a control wheel in accordance with some embodiments of the invention.
Figure 18:
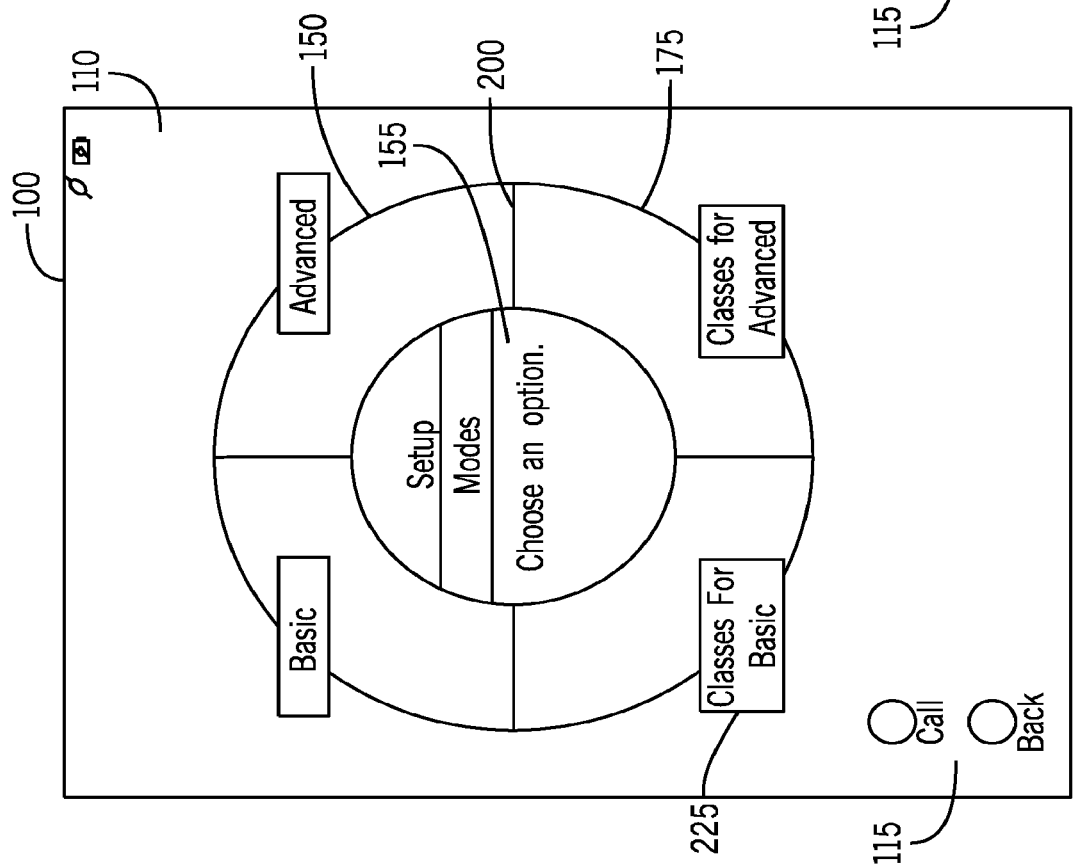
FIG. 18 illustrates a display with a user interface for controlling a dental laser station displaying a control wheel in accordance with some embodiments of the invention.

In some embodiments of the invention, the user can use the control wheel 150 to set or update various setting of the dental laser station 10. For example, referring to FIG. 14 illustrating a display 100 with a user interface 110 for controlling a dental laser station 10, and FIG. 15 illustrating a display 100 with a user interface 110 for controlling a dental laser station 10, the control wheel 150 can be used to access, set or adjust one or more setting of the dental laser station 10 following a user selection of any one of the segments 200 as shown. Further, as an example embodiment, FIG. 16 illustrates a display 100 with a user interface 110 for controlling a dental laser station 10 displaying a control wheel 150 configured to enable a user to change a user configuration setup in accordance with some embodiments of the invention. For example, following a user selection of the segment 200 including a banner content 225 of "add a new user", a user can setup or update the dental laser station 10 with a new user. For example, FIG. 17 illustrates a display 100 with a user interface 110 for controlling a dental laser station 10 displaying an entry screen with data entry 170 configured for entry of a username of a new user. In some further embodiments, users can be renamed, deleted, or cleared. Other example embodiments including setup configurations are shown in FIG. 18, illustrating a display 100 with a user interface 110 for controlling a dental laser station 10, and FIG. 19 illustrating a display 100 with a user interface 110 for controlling a dental laser station 10 displaying a control wheel 150 in accordance with some embodiments of the invention.

Figure 21:
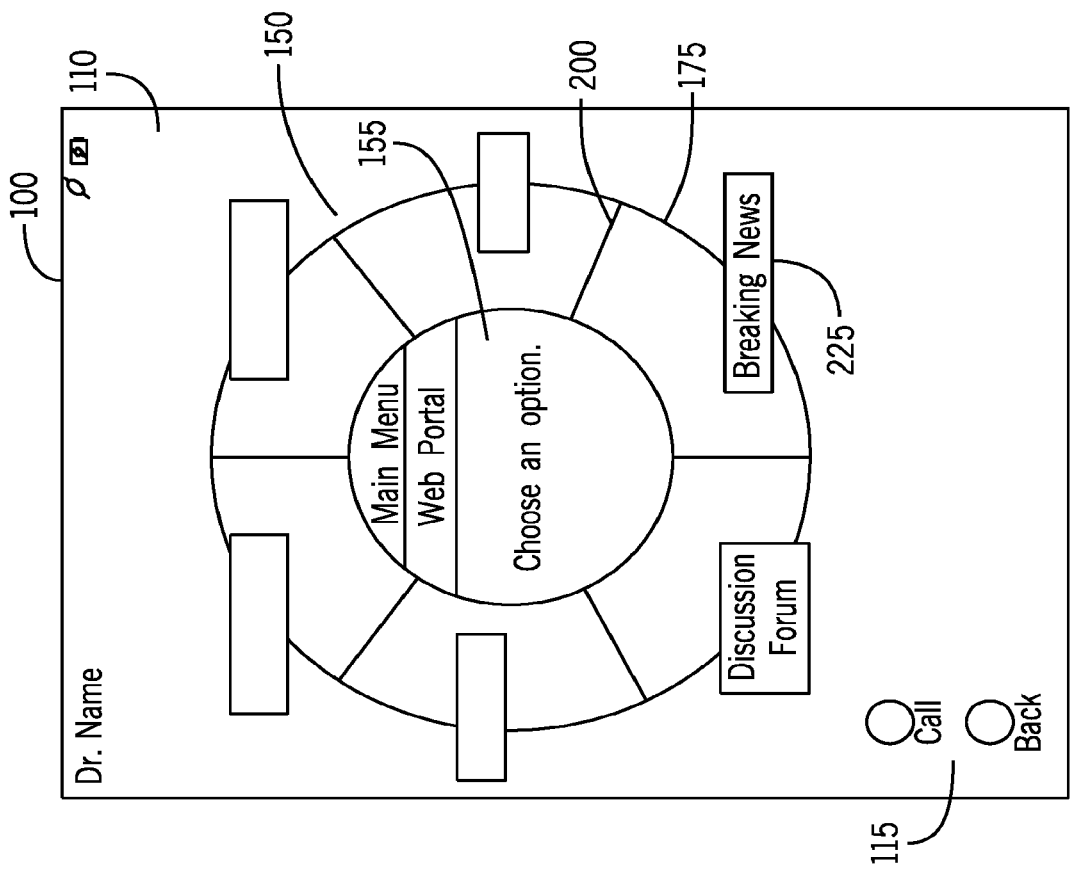
FIG. 21 illustrates a display with a user interface for controlling a dental laser station displaying a control wheel in accordance with some embodiments of the invention.
Figure 20:
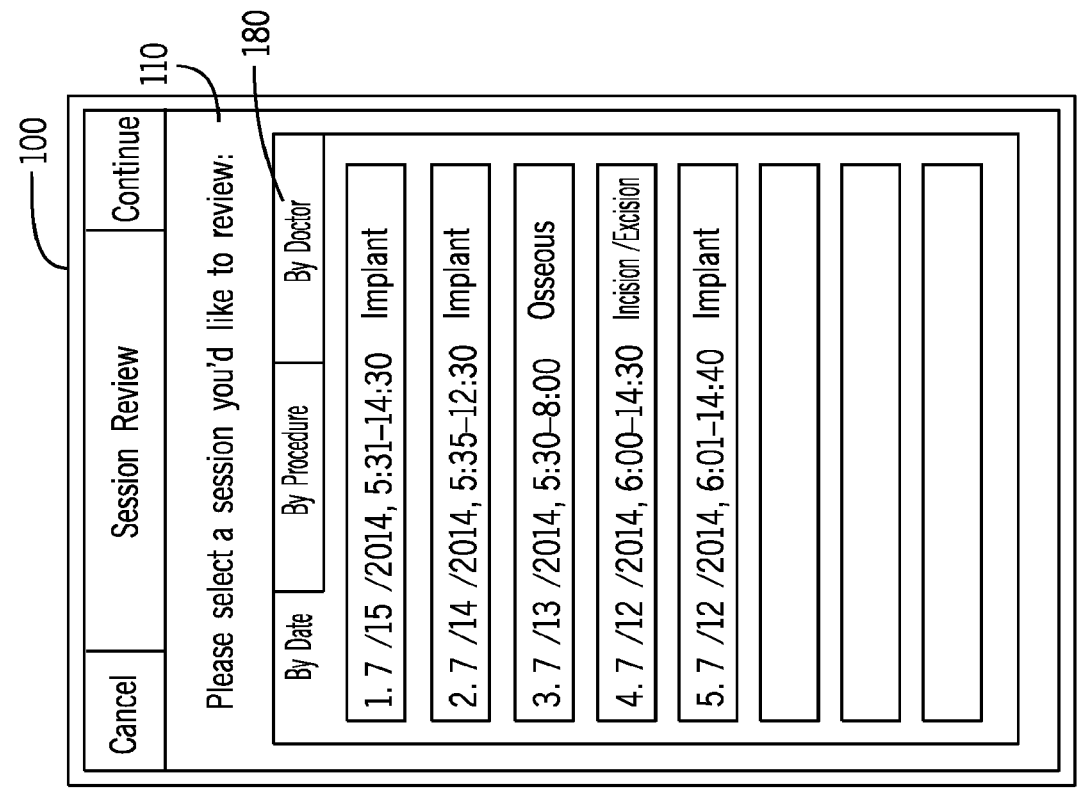
FIG. 20 illustrates a display with a user interface for controlling a dental laser station displaying a session menu in accordance with some embodiments of the invention.

In some embodiments, the user can select a session to review or enter a web portal. For example, FIG. 20 illustrates a display 100 with a user interface 110 for controlling a dental laser station 10 displaying a session menu 180 in accordance with some embodiments of the invention. As illustrated, the session menu 180 can enable a user to review sessions by date, by procedure, and/or by doctor. FIG. 21 illustrates a display 100 with a user interface 110 for controlling a dental laser station 10 displaying a control wheel 150 configured with web portal access in accordance with some embodiments of the invention. For example, in some embodiments, the user can use the control wheel 150 to access a discussion forum or breaking news in a web portal by selecting at least one of the segments 200.

Figure 23:
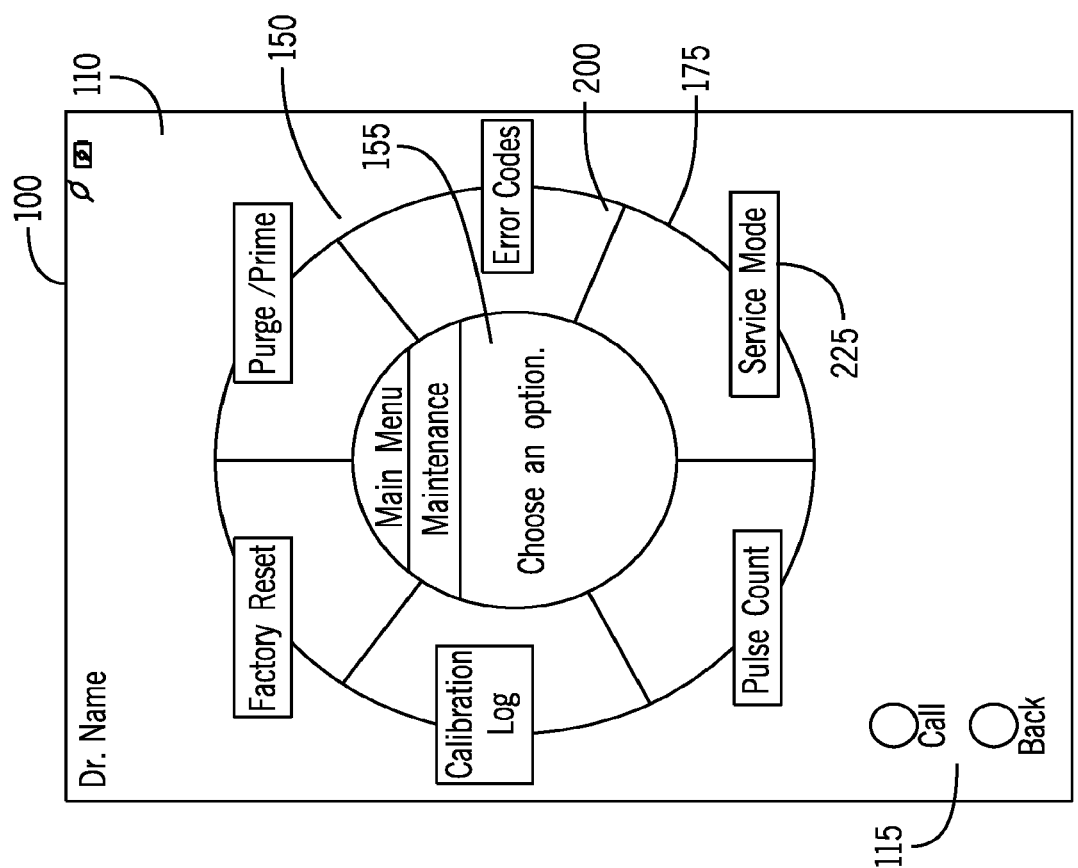
FIG. 23 illustrates a display with a user interface for controlling a dental laser station displaying a control wheel in accordance with some embodiments of the invention.
Figure 22:
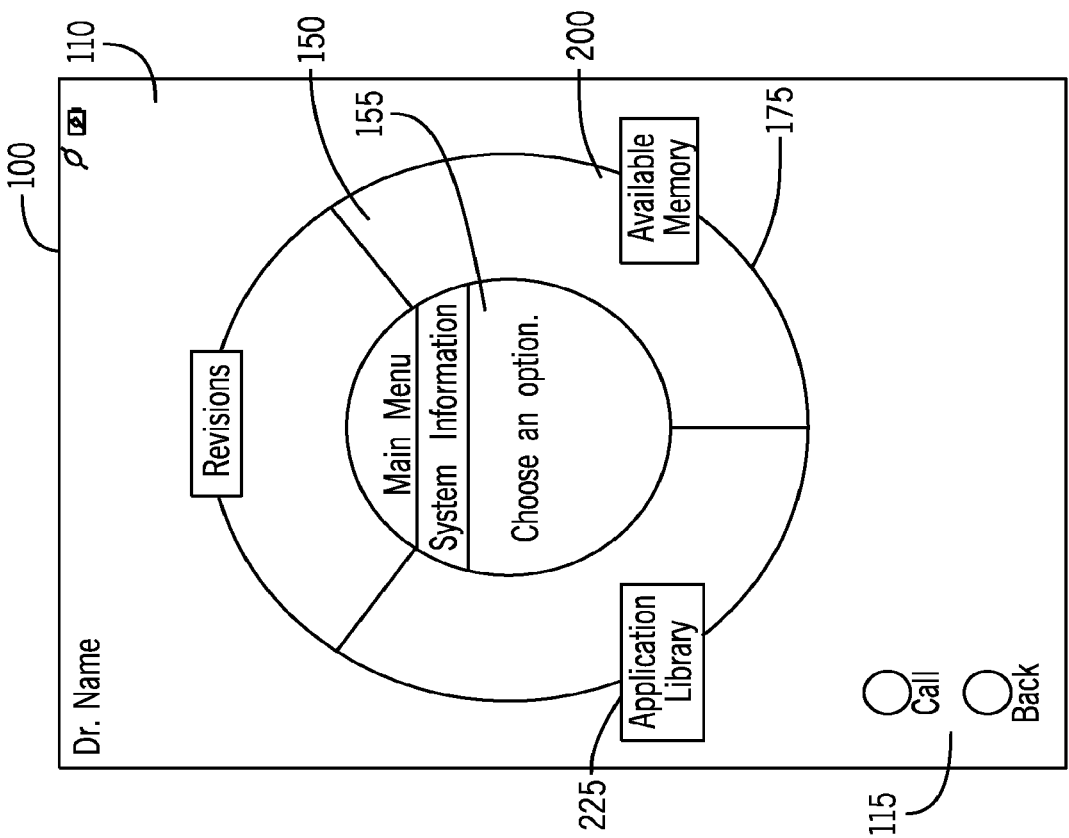
FIG. 22 illustrates a display with a user interface for controlling a dental laser station displaying a control wheel in accordance with some embodiments of the invention.

In some other embodiments of the invention, the user can use the control wheel 150 to initiate or check system and maintenance, or to enter a service mode. For example, FIG. 22 illustrates a display 100 with a user interface 110 for controlling a dental laser station 10 displaying a control wheel 10 configured to access and/or update system information in accordance with some embodiments of the invention. Further, FIG. 23 illustrates a display 100 with a user interface 110 for controlling a dental laser station 10 displaying a control wheel 150 configured with options related to maintenance in accordance with some embodiments of the invention. Further, FIG. 24 illustrates a display 100 with a user interface 110 for controlling a dental laser station 10 displaying a control wheel 150 configured for a service mode in accordance with some embodiments of the invention.

Embodiments of the invention described herein can include a display or access to various menus, legends, and information displays describing or related to any descriptions, symbols and graphics displayed by the dental laser station 10 including any device coupled to the docking station 20, and any mobile interface 25. For example, FIG. 25 illustrates an icon legend 185 of a display 100 with a user interface 110 for controlling a dental laser station 10 in accordance with some embodiments of the invention. Further, FIG. 26 illustrates handpieces and tips selection menu 190 of a display 100 with a user interface 110 for controlling a dental laser station 10 in accordance with some embodiments of the invention. FIG. 27 illustrates a key menu with key legend 195 of a display 100 with a user interface 110 for controlling a dental laser station 10 in accordance with some embodiments of the invention, and FIG. 28 illustrates an information menu including an input legend 197 of a display 100 with a user interface 110 for controlling a dental laser station 10 in accordance with some embodiments of the invention. In some embodiments, the display 100 can display any of the information including text, symbols and graphics shown in FIGS. 25-28. In other embodiments, the information including text, symbols and graphics shown in FIGS. 25-28 can be including in documentation provided to the user and/or printed on a label or other attachment coupled to the dental laser station 10.

Figures 29, 30:
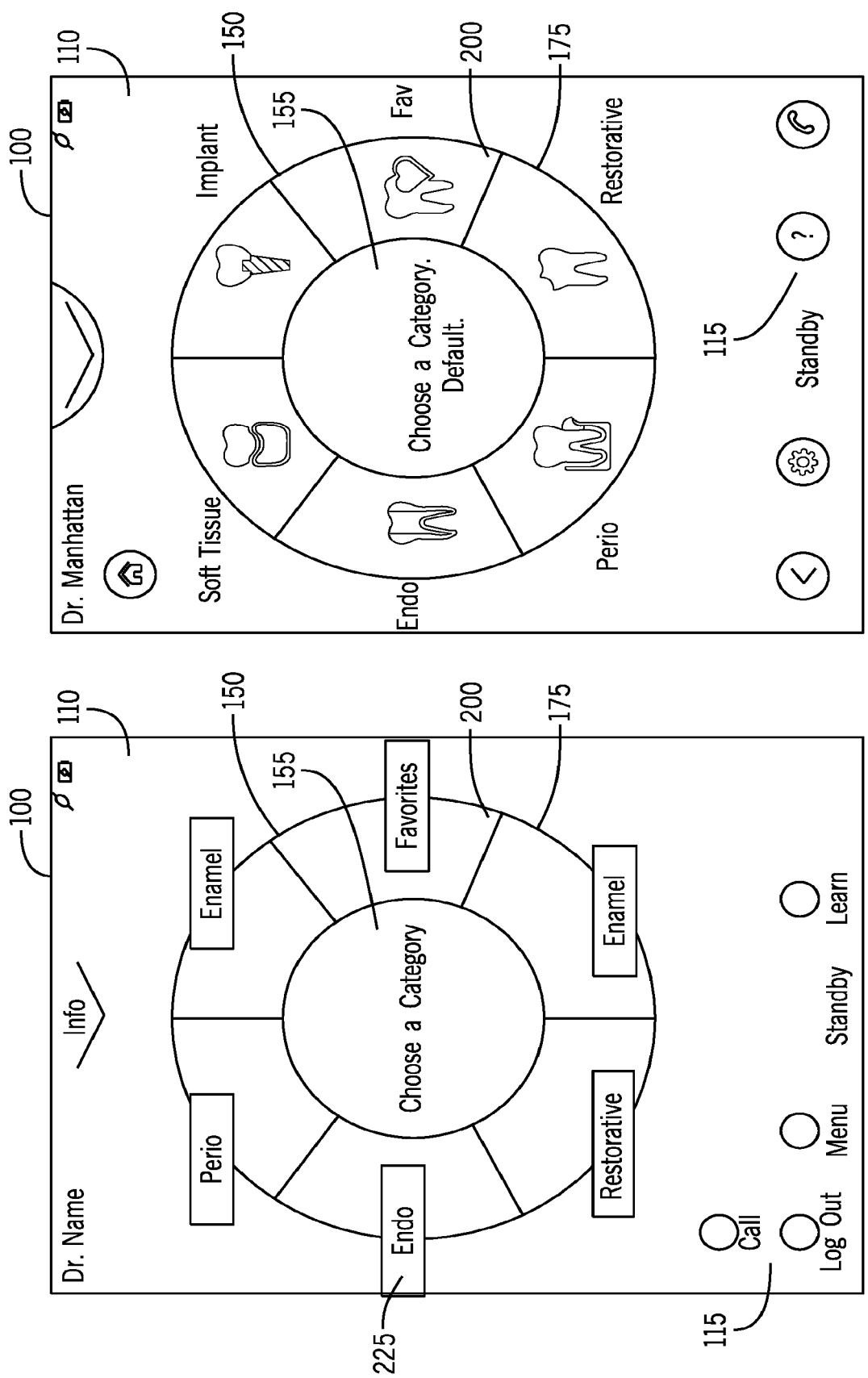
FIG. 29 illustrates a display with a user interface for controlling a dental laser station displaying a control wheel in accordance with some embodiments of the invention.
FIG. 30 illustrates a display with a user interface for controlling a dental laser station displaying a control wheel in accordance with some embodiments of the invention.
Figure 38:
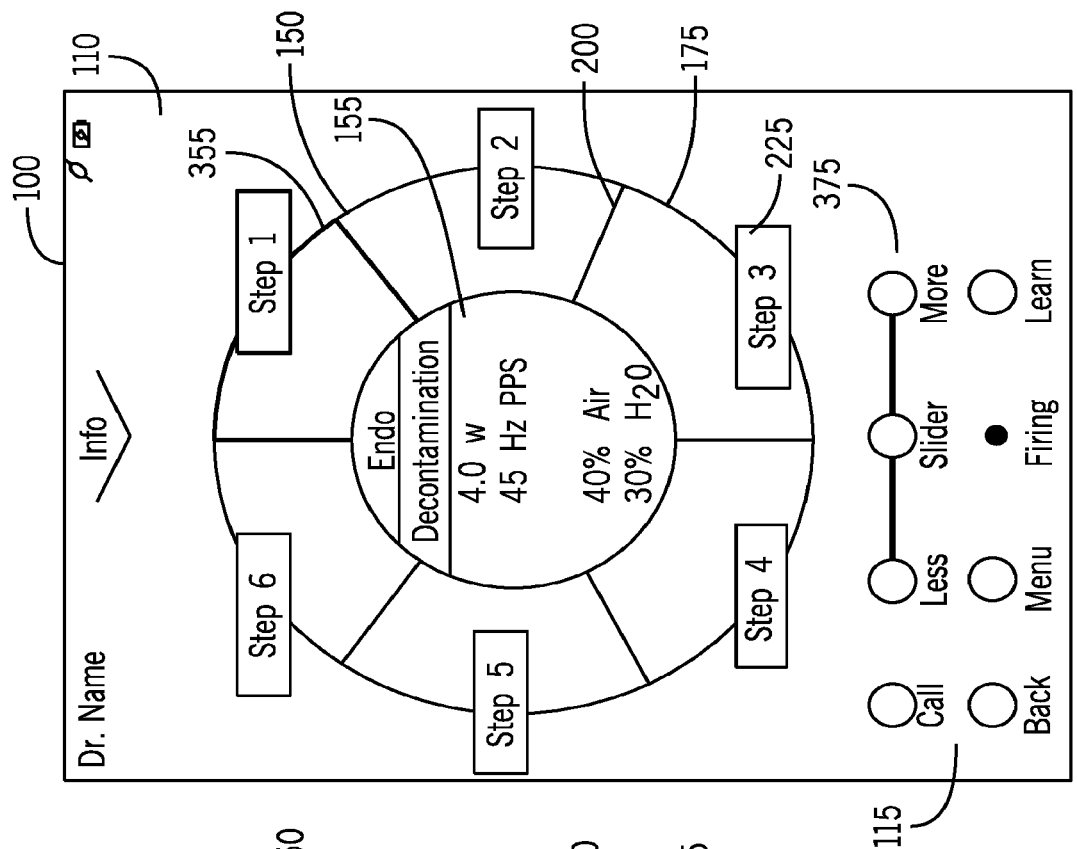
Figure 37:
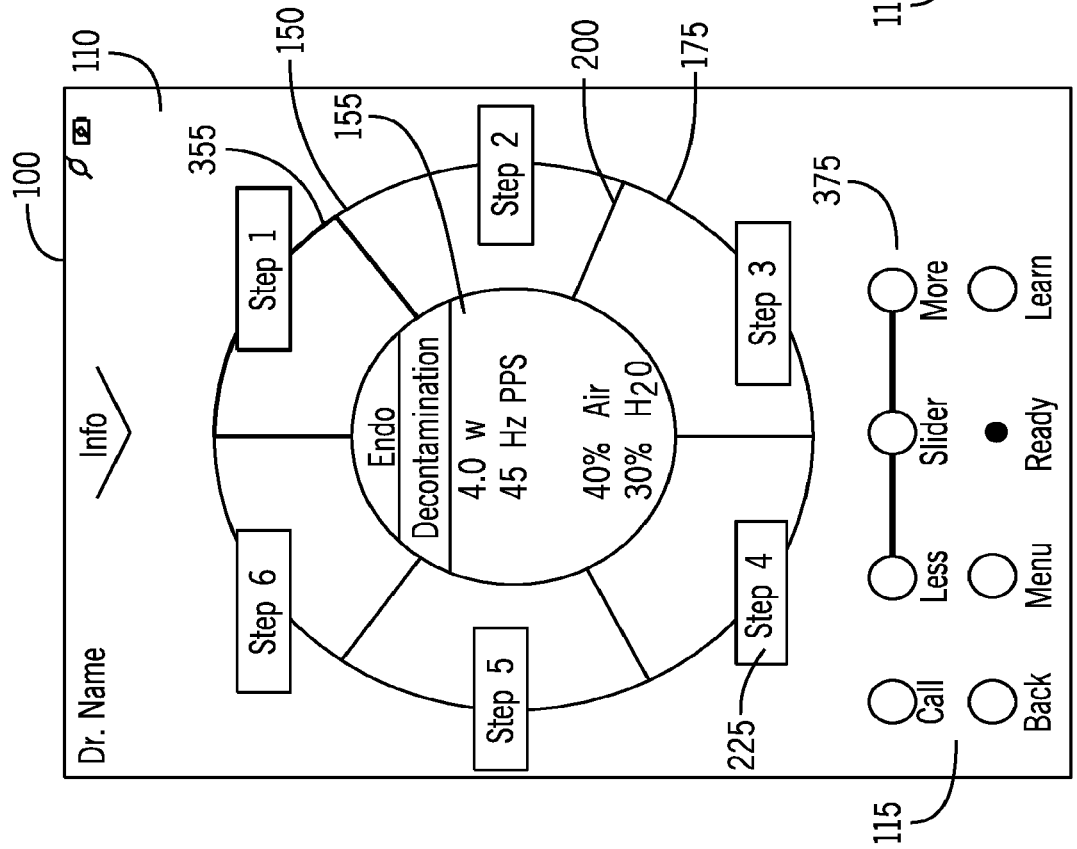
Figure 40:
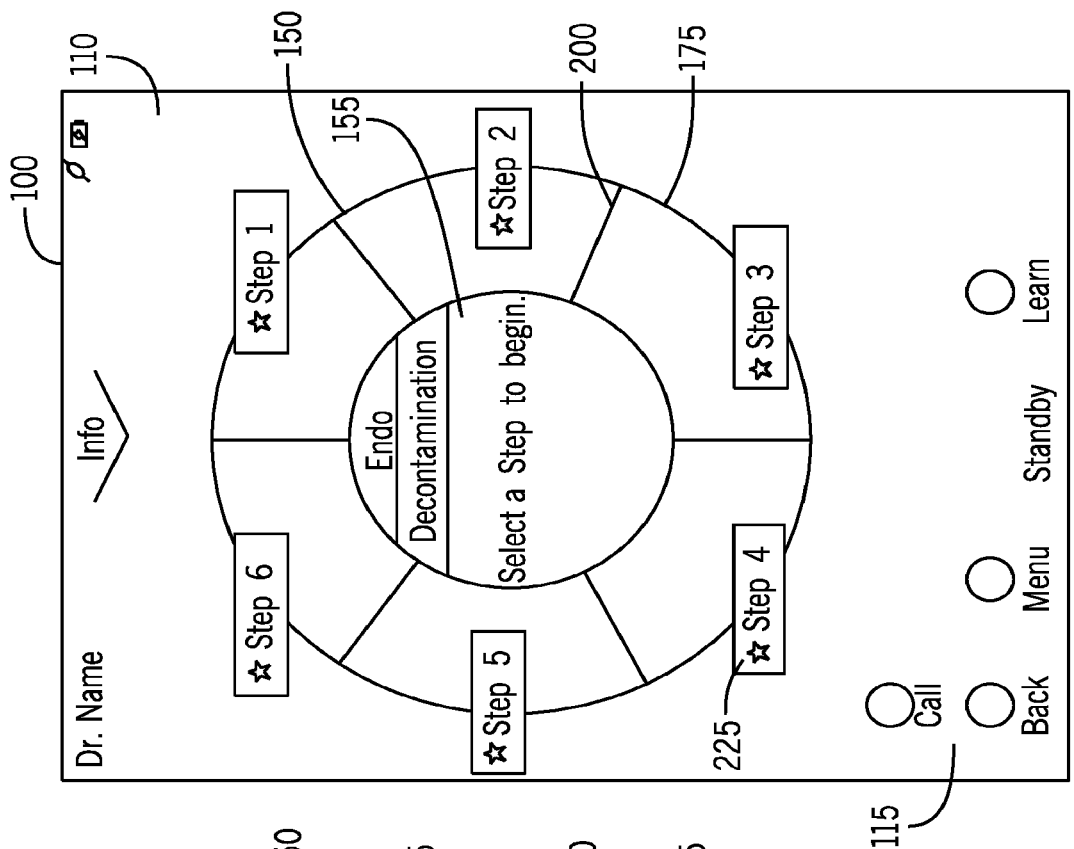
Figure 39:
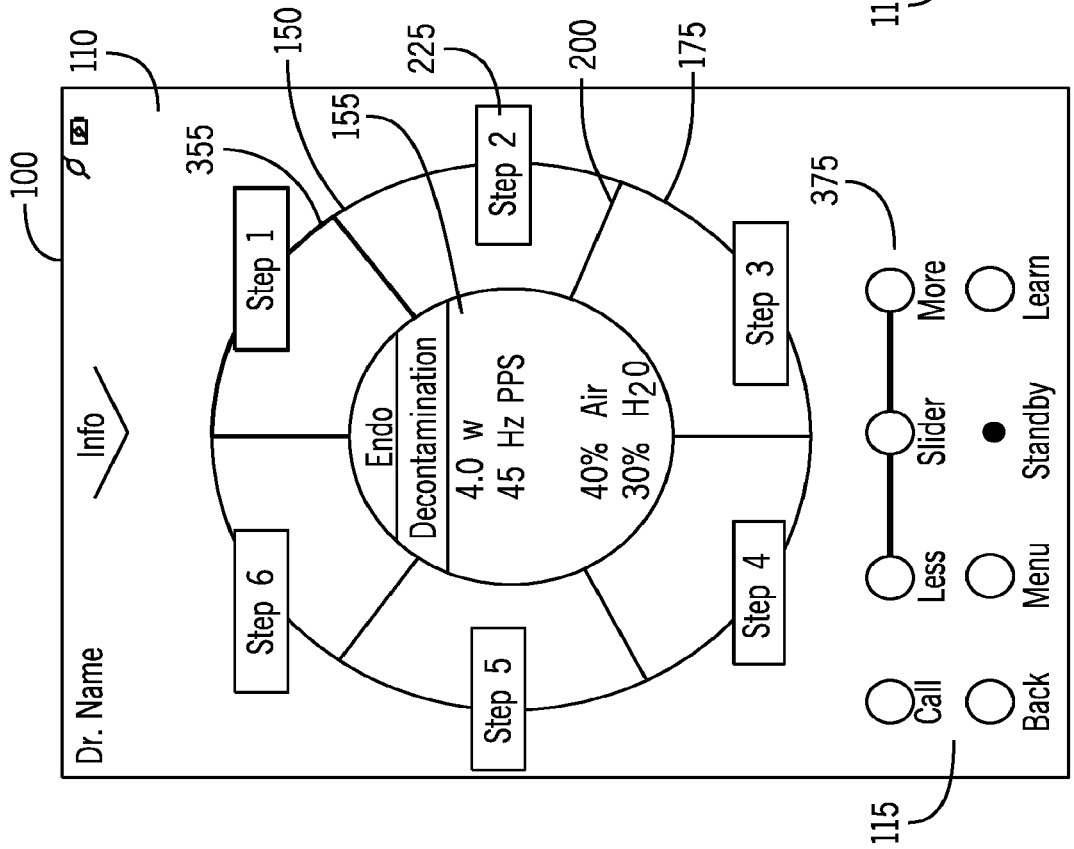

In some embodiments of the invention, a user can initiate a treatment or procedure category. For example, FIGS. 29-30 illustrate example display 100 with a user interface 110 for controlling a dental laser station 10 displaying a control wheel configured to enable a user to select at least on category in accordance with some embodiments of the invention. In some embodiments, the selected category can be highlighted in the control wheel 150. For example, FIG. 31 illustrates a display 100 with a user interface 110 for controlling a dental laser station 10 displaying a control wheel 150 including a highlighted segment 200a in accordance with some embodiments of the invention.

As an additional example, the first display 155 of FIG. 31 displays a message alerting the user is not authorized to use the chosen category. In some embodiments, after a user selects a category, the user can use the control wheel 150 to select a specific procedure. For example, FIG. 32 illustrates a display 100 with a user interface 110 for controlling a dental laser station 10 displaying a control wheel 150 configured to enable a user to select at least one procedure in accordance with some embodiments of the invention.

As the user prepares to perform a selected procedure, the display 100 can enable the user to define specific tools including specific handpieces and tips. For example, FIG. 33 illustrates a display 100 with a user interface 110 for controlling a dental laser station 10 displaying a tip selection menu in accordance with some embodiments of the invention. For example, the display 100 can be configured to display a user interface 110 including a tool display 300 comprising tip selection icons 305. In some embodiments, the user interface 110 can show the currently selected tool (current tool 315) and/or a recommended tool based on the selected procedure (recommended tool 320).

FIGS. 34-47 illustrate displays 100 with example user interfaces 110 for controlling a dental laser station 10 displaying control wheels 150 configured for an example procedure in accordance with some embodiments of the invention. The example procedure comprises a series of selected steps for a decontamination within an endodontic category, however other example procedures can include display similar to those displayed in FIGS. 34-47. The control wheel 150 can be used to select one or more steps of the procedure. For example, as shown in FIGS. 36-39, the control wheel 150 can highlight selected step 1 (shown as highlighted segment 355). Further, the control wheel 150 can show a parameter display 350 indicating one or more parameters of the dental laser station 10. In some embodiments, one or more of the parameters can be modified using a slider bar 375 displayed in the user interface 110. Moreover, the status of the dental laser can be displayed as an indicator within the user interface 110, for example showing dental laser "ready", "firing", or in "standby" mode.

Figure 43:
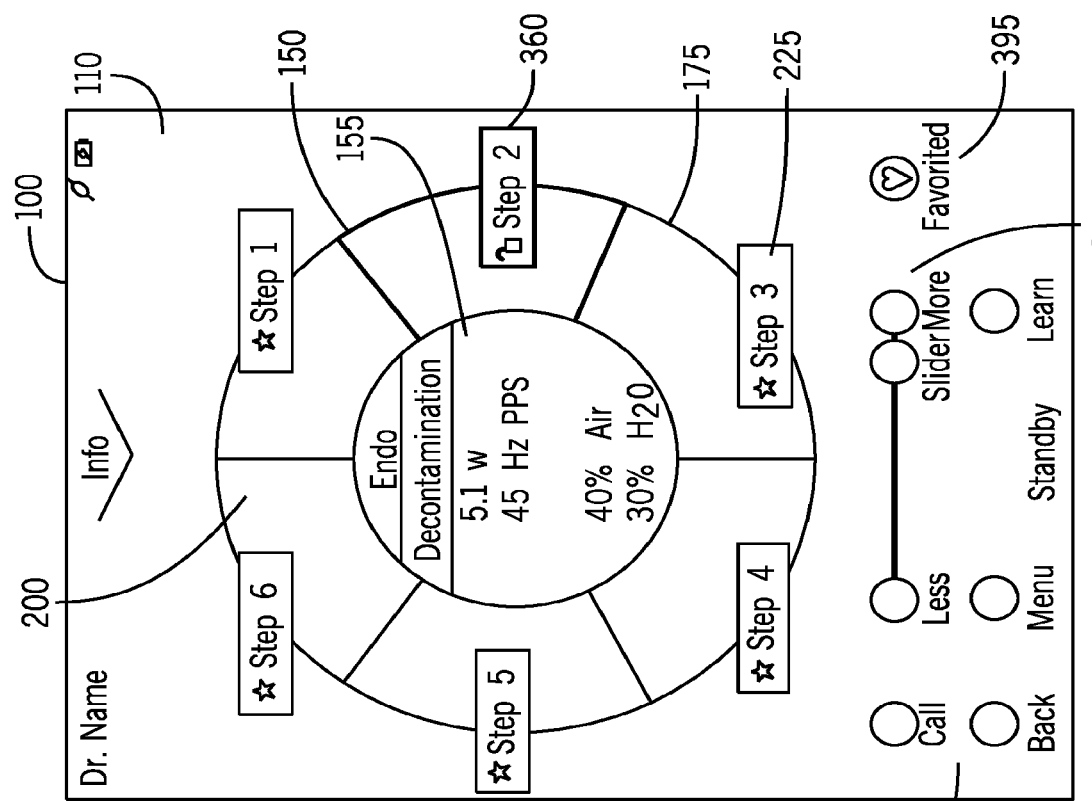
Figure 44:
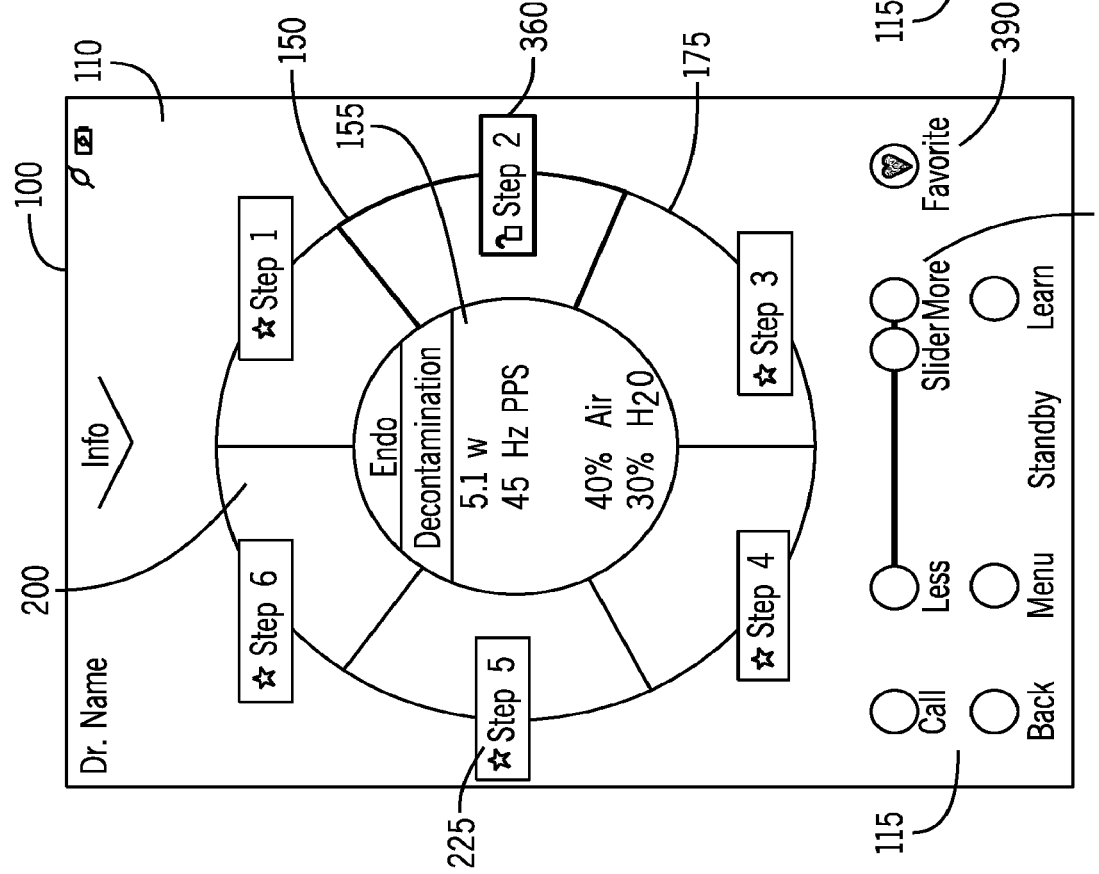

Referring to FIGS. 40-47, following the completion of a first step, a user can proceed with any further steps of a procedure. For example, as depicted in FIGS. 41-47, a user can proceed with a selected second step 360. Further, as shown in FIGS. 41-43, a user can be provided with an option to select a favorite procedure and/or step of a procedure (shown as favorite icon 390), and following selection, a favorited icon 395 can be displayed in the user interface 110. Further, as depicted in FIG. 45, showing a display 100 with a user interface 110 for controlling a dental laser station 10, in some embodiments, the control wheel 150 can comprise a saved step selection 215 to enable a user to save a selected step.

Figure 48:
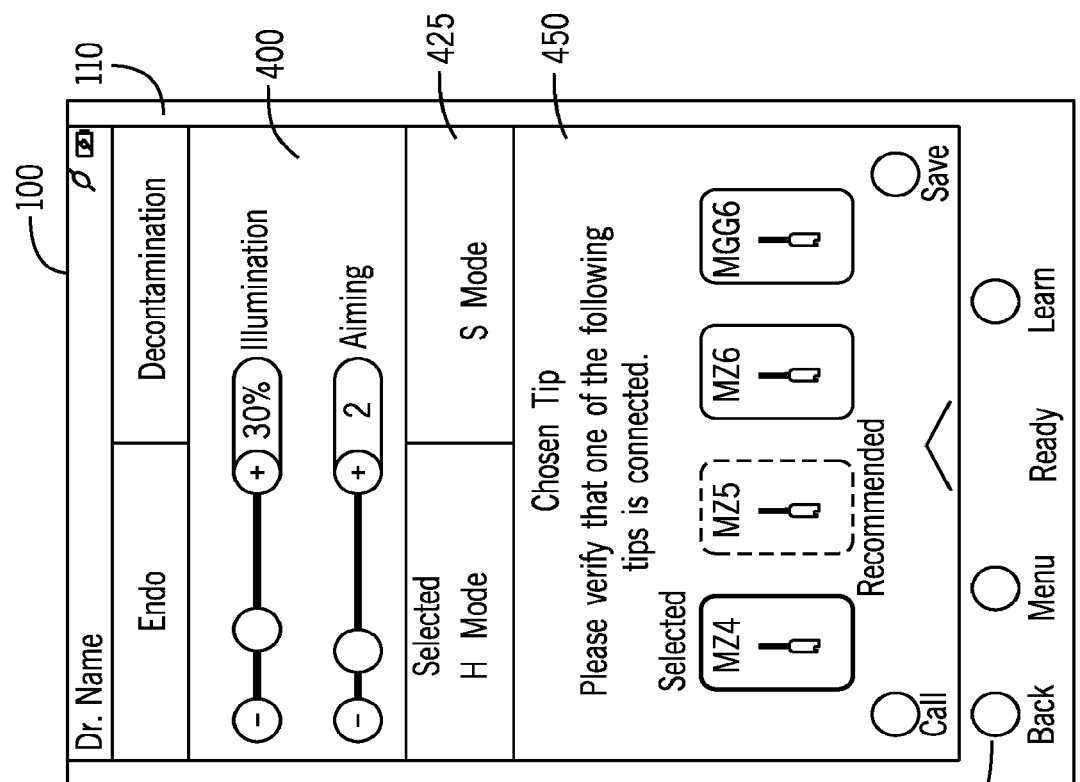
FIG. 48 illustrates a display with a user interface for controlling a dental laser station including an example parameter display in accordance with some embodiments of the invention.
Figure 47:
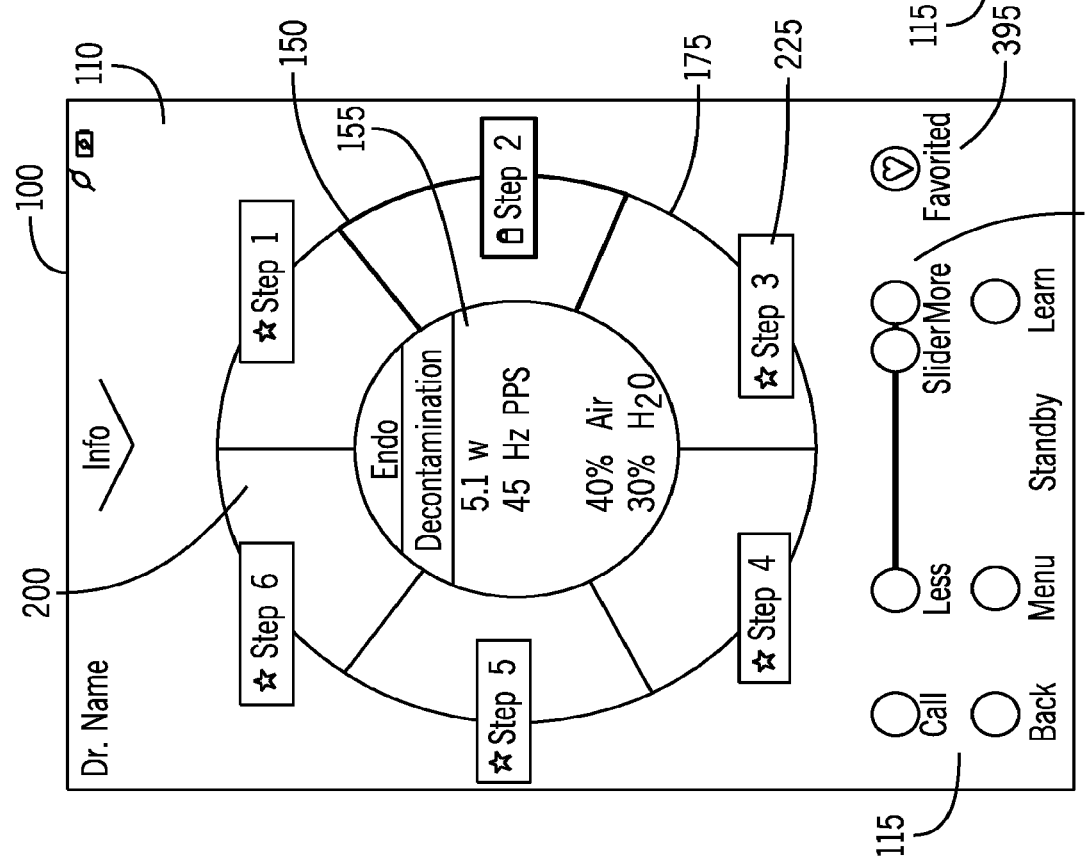
Figures 49, 50:
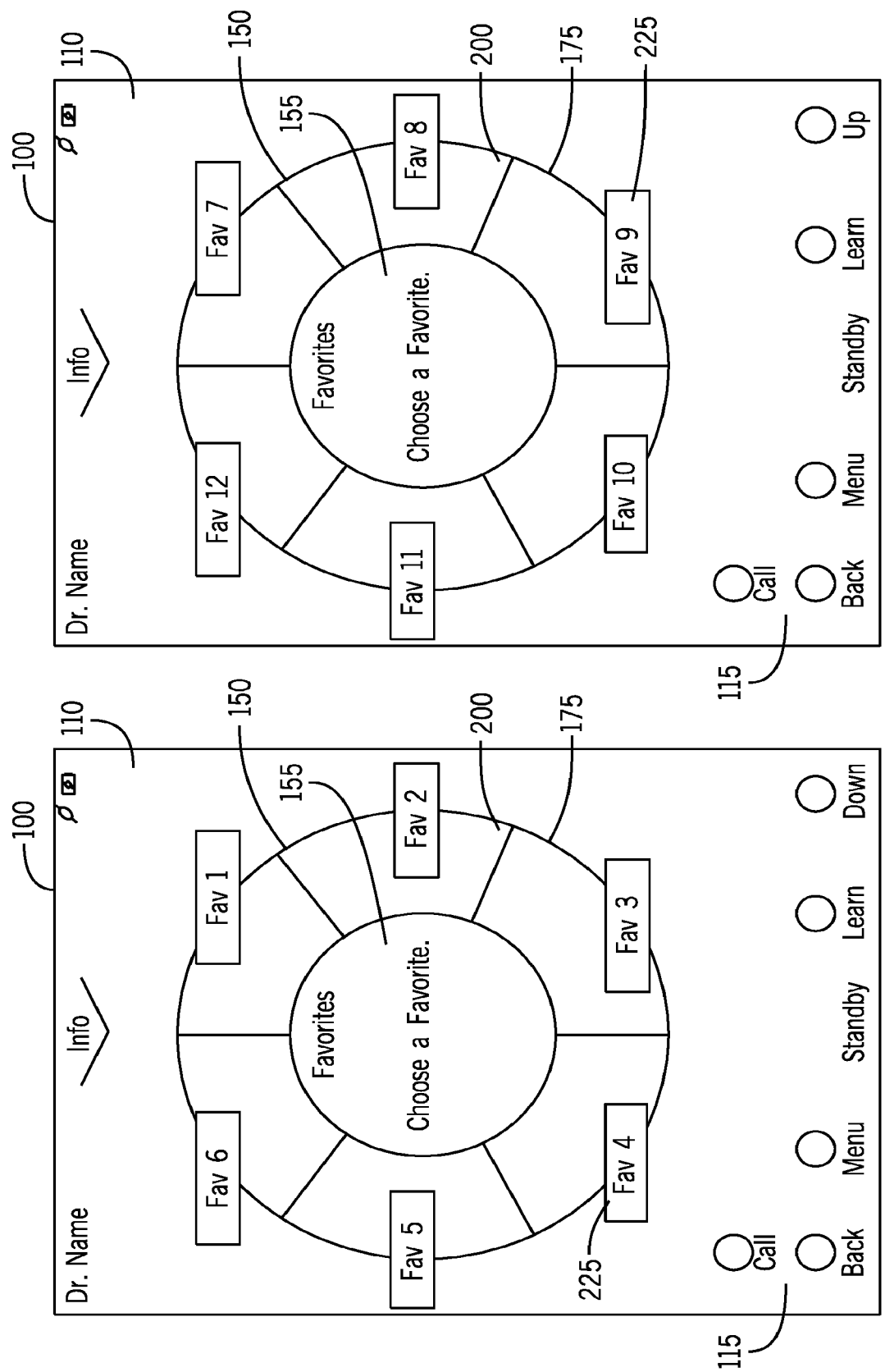

In some embodiments, tool parameters can be shown and changed using the user interface 110. For example, FIG. 48 illustrates a display 100 with a user interface 110 for controlling a dental laser station 10 including an example parameter display in accordance with some embodiments of the invention. In some embodiments, the user interface can include a control display 400, and/or mode display 425, and/or chosen tip display 450. Further, in some embodiments, the chosen tip display 450 can include a tip verification display 475 depicting a current tip 480, and a recommended tip 485.

FIGS. 49-55 illustrate displays 100 with user interfaces 110 for controlling a dental laser station 10 displaying example control wheels 150 in accordance with some embodiments of the invention. For example, FIGS. 49-52 illustrate displays 100 with user interfaces 110 configured for favorites selection using the control wheel 150 for controlling a dental laser station 10 displaying a control wheel 150 in accordance with some embodiments of the invention. For example, FIG. 51 shows a selected segment 210 identifying a user-selected favorite. Further, in some embodiments, the user interface can display information related to a specific tool or tip that is in use and/has been selected. For example, FIG. 53 illustrates a display 100 with a user interface 110 for controlling a dental laser station 10 displaying a control wheel 150 that includes a tip marker 308.

Figure 58:
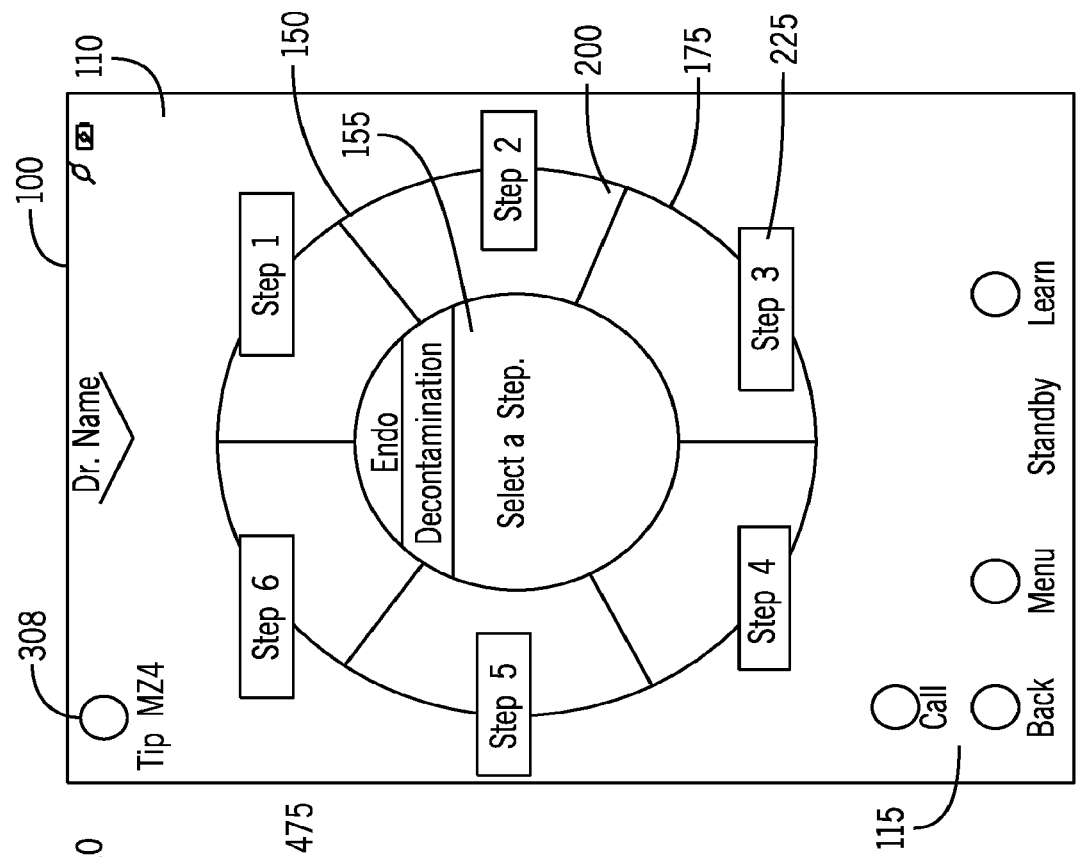
Figure 57:
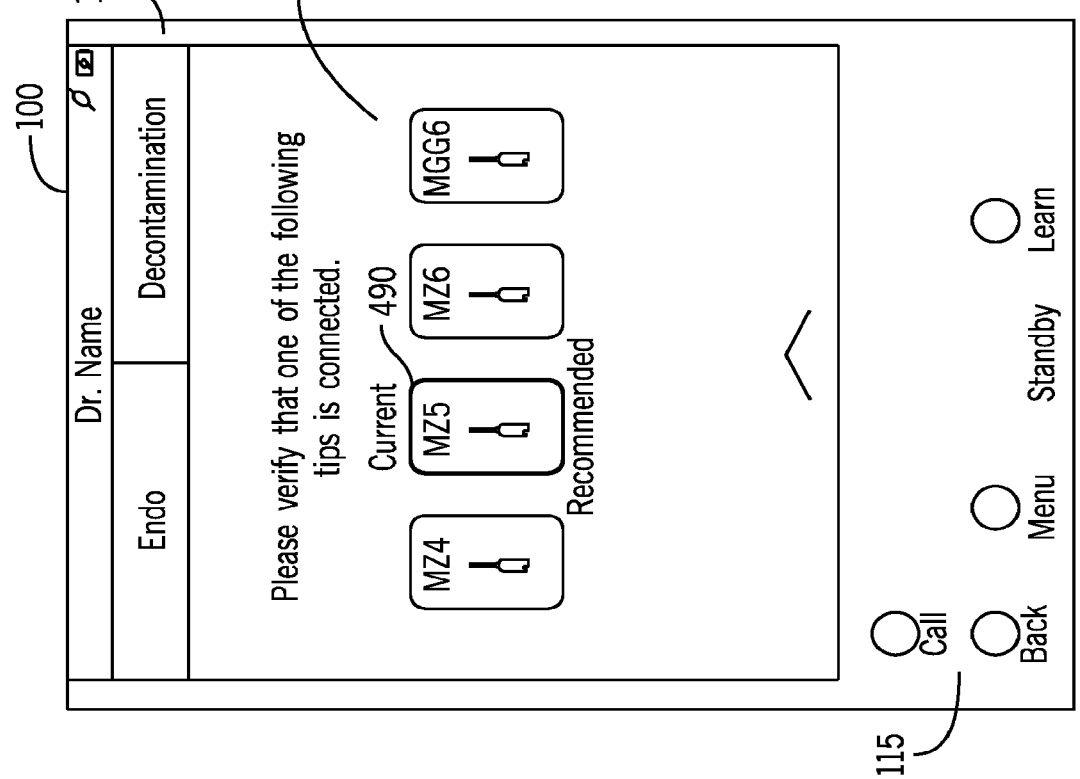
Figures 59, 60:
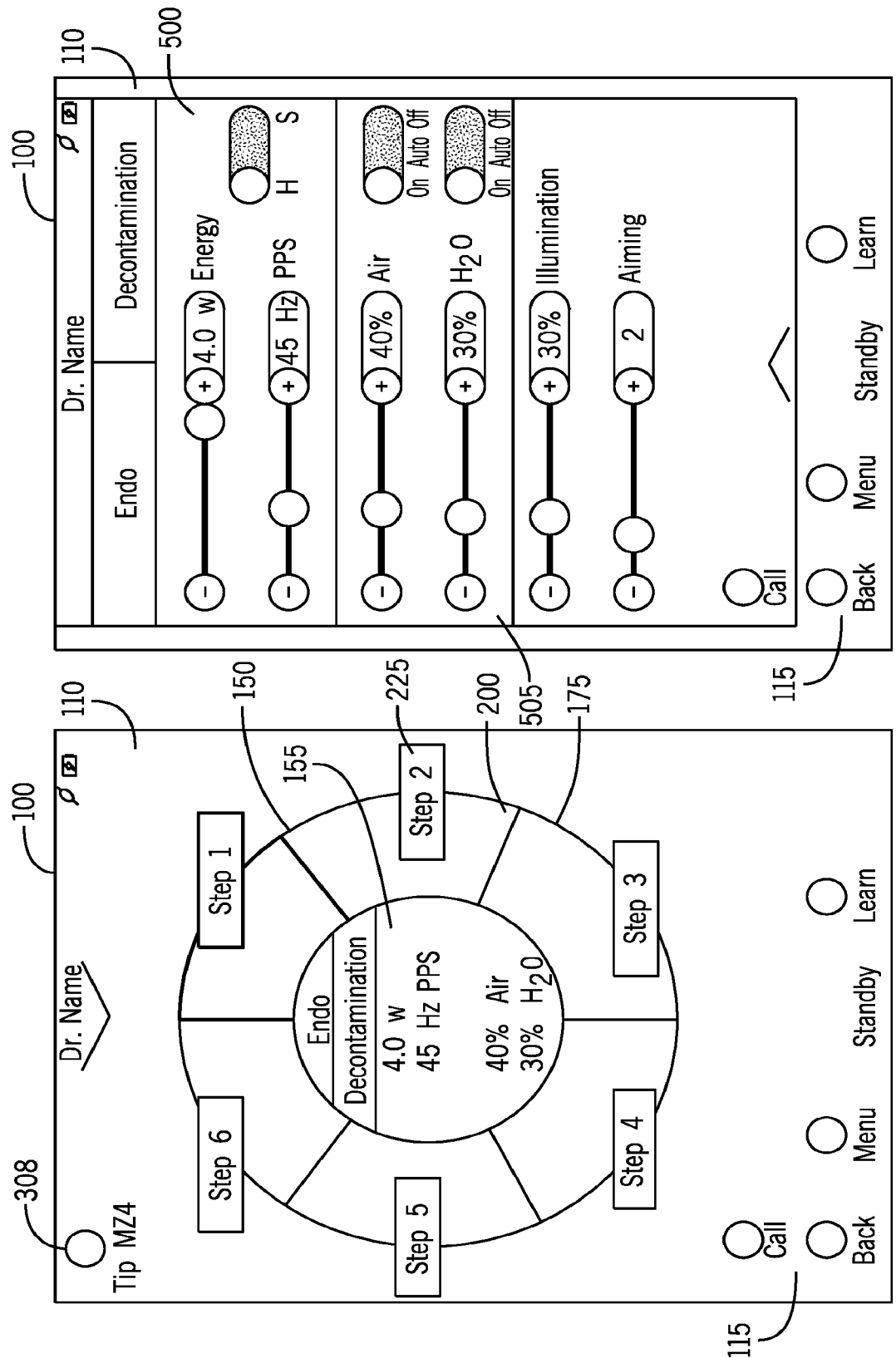

In some further embodiments, the user can encouraged or asked to change a tip type. For example, FIG. 55 illustrates a display 100 with a user interface 110 for controlling a dental laser station 10 displaying a control wheel 150 in accordance with some embodiments of the invention that includes a message window 230 displaying a request for the used to change a tip type. FIGS. 56-57 illustrate displays 100 with user interfaces 110 for controlling a dental laser station 10 including an example tip check displays with FIG. 56 showing current tip 480 and recommended tip 485, and FIG. 57 showing current/recommended tip 490. FIGS. 58-59 illustrate displays 100 with user interfaces 110 for controlling a dental laser station 10 displaying example control wheels 150 including a notification of the tip type (shown as tip marker 308) in accordance with some embodiments of the invention.

FIGS. 60-61 illustrate displays 100 with user interfaces 110 for controlling a dental laser station 10 including control parameter selection tools in accordance with some embodiments of the invention. For example, user interface 110 can include a control display 500 configured to monitor various parameters of the dental laser station 10. In some embodiments, one or more slider bars 505 can be displayed to enable the user to change one or more of the parameters displayed in the control display 500.

FIG. 62 illustrates a display 100 with a user interface 110 for controlling a dental laser station display 10 an example control wheel 150 in accordance with some other embodiments of the invention. In some embodiments, any one of the segments 200 can comprise one or more graphic icons 227 that can be configured by the dental laser station 10. Further, in some embodiments, the user interface 110 can also include at least one control slider 117 that can be configured to control at least one parameter of the dental laser station 10. Including any parameters displayed in the first display 155.

Figure 63:
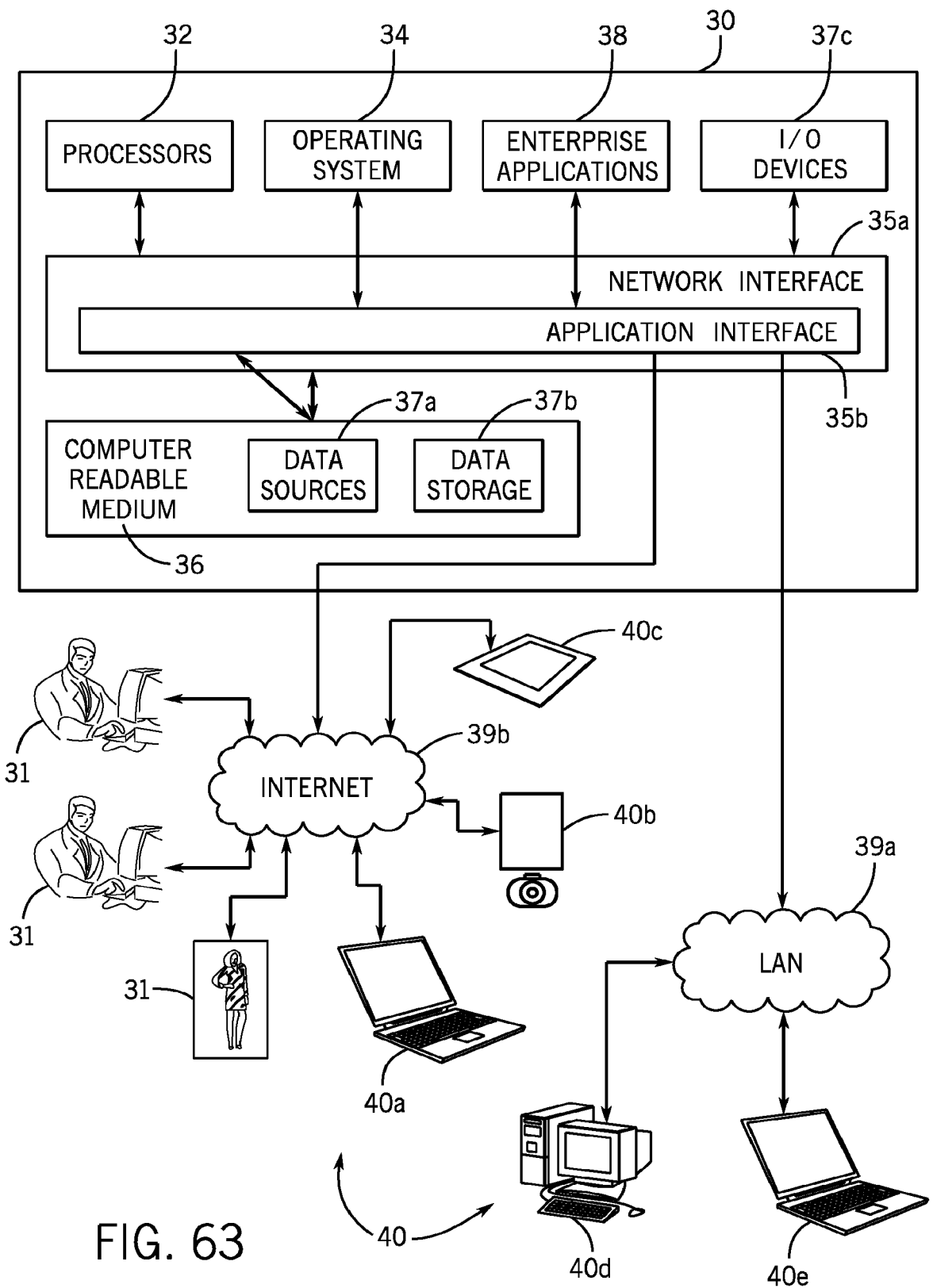
FIG. 63 illustrates a computer system for implementing displays including user interfaces for controlling a dental laser station in accordance with some embodiments of the invention.

FIG. 63 illustrates a computer system 30 for implementing displays with user interfaces for controlling a dental laser station in accordance with some embodiments of the invention. In some embodiments of the invention, computer system 30 comprises operating and processing modules of a dental laser station control system and method for a display with a user interface to enable a user to control one or more dental laser stations. In some embodiments, the computer system 30 can process one or more software modules of the aforementioned dentistry control system and method and display information related to dental devices within at least one user interface. Further, in some embodiments, using the computer system 30, the dentistry control system and method can manage the organization of data and data flow between the various components of the dentistry control system and method.

In some embodiments, the system 30 can include at least one computing device, including one or more processors 32. Some processors 32 can include processors 32 residing in one or more conventional server platforms. The system 30 can include a network interface 35a and an application interface 35b coupled to at least one processors 32 capable of running at least one operating system 34. Further, the system 30 can include a network interface 35a and an application interface 35b coupled to at least one processors 32 capable of running one or more of the software modules (e.g., enterprise applications 38). Some embodiments of the invention also relate to a device or an apparatus for performing these operations. The apparatus can be specially constructed for the required purpose, such as a special purpose computer. When defined as a special purpose computer, the computer can also perform other processing, program execution or routines that are not part of the special purpose, while still being capable of operating for the special purpose. Alternatively, the operations can be processed by a general purpose computer selectively activated or configured by one or more computer programs stored in the computer memory, cache, or obtained over a network. When data are obtained over a network the data can be processed by other computers on the network, e.g. a cloud of computing resources.

With the above embodiments in mind, it should be understood that the invention can employ various computer-implemented operations involving dentistry control data stored in computer systems. Moreover, the above-described databases and models throughout the dentistry control can store analytical models and other data on computer-readable storage media within the system 30 and on computer-readable storage media coupled to the system 30. In addition, the above-described applications of the dentistry control system can be stored on computer-readable storage media within the system 30 and on computer-readable storage media coupled to the system 30. These operations are those requiring physical manipulation of physical quantities. Usually, though not necessarily, these quantities take the form of electrical, electromagnetic, or magnetic signals, optical or magneto-optical form capable of being stored, transferred, combined, compared and otherwise manipulated.

Some embodiments include the system 30 comprising at least one computer readable medium 36 coupled to at least one data storage device 37b, and/or at least one data source 37a, and/or at least one input/output device 37c. In some embodiments, the invention embodied by the dentistry control system can also be embodied as computer readable code on a computer readable medium 36. The computer readable medium 36 can be any data storage device that can store data, which can thereafter be read by a computer system (such as the system 30). Examples of the computer readable medium 36 can include hard drives, network attached storage (NAS), read-only memory, random-access memory, FLASH based memory, CD-ROMs, CD-Rs, CD-RWs, DVDs, magnetic tapes, other optical and non-optical data storage devices, or any other physical or material medium which can be used to tangibly store the desired information or data or instructions and which can be accessed by a computer or processor (including processors 32).

In some embodiments of the invention, the computer readable medium 36 can also be distributed over a conventional computer network via the network interface 35a so that the dentistry control system embodied by the computer readable code can be stored and executed in a distributed fashion. For example, in some embodiments, one or more components of the system 30 can be tethered to send and/or receive data through a local area network ("LAN") 39a. In some further embodiments, one or more components of the system 30 can be tethered to send or receive data through an internet 39b (e.g., a wireless internet). In some embodiments, at least one software application 38 running on one or more processors 32 can be configured to be coupled for communication over a network 39a, 39b. In some embodiments, one or more components of the network 39a, 39b can include one or more resources for data storage, including any other form of computer readable media beyond the media 36 for storing information and including any form of computer readable media for communicating information from one electronic device to another electronic device.

In some embodiments, the network 39a, 39b can include wide area networks ("WAN"), direct connections (e.g., through a universal serial bus port) or other forms of computer-readable media 36, or any combination thereof. Further, in some embodiments, one or more components of the network 39a, 39b can include a number of client devices which can be personal computers 40 including for example desktop computers 40d, laptop computers 40a, 40e, digital assistants and/or personal digital assistants (shown as 40c), cellular phones or mobile phones or smart phones (shown as 40b), pagers, digital tablets, internet appliances, and other processor-based devices. In general, a client device can be any type of external or internal devices such as a mouse, a CD-ROM, DVD, a keyboard, a display, or other input or output devices 37c. In some embodiments, various other forms of computer-readable media 36 can transmit or carry instructions to a computer 40, including a rsecond, private or public network, or other transmission device or channel, both wired and wireless. The software modules 38 can be configured to send and receive data from a database (e.g., from a computer readable medium 36 including data sources 37a and data storage 37b that can comprise a database), and data can be received by the software modules 38 from at least one other source.

In some embodiments, at least one of the software modules 38 can be configured within the system 30 to output data to at least one user 31 via at least one digital display (e.g., to a computer 40 comprising a digital display). In some embodiments, the system 30 as described can enable one or more users 31 to receive, analyze, input, modify, create and send data to and from the system 30, including to and from one or more enterprise applications 38 running on the system 30. Some embodiments include at least one user 31 coupled to a computer 40 accessing one or more modules of the dentistry control system including at least one enterprise applications 38 via a stationary I/O device 37c through a LAN 39a. In some other embodiments, the system 30 can enable at least one user 31 (through computer 40) accessing enterprise applications 38 via a stationary or mobile I/O device 37c through an internet 39a.

In some embodiments, the software modules 38 can include a server-based software platform that can include dentistry control software modules suitable for hosting at least one user 31 account and at least one patient account or record. Further, some embodiments of invention includes the software modules 38 that can include at least one server-based software platform that can include dentistry control software modules suitable for hosting at least at least one patient account or record. In some embodiments, using the system 30, the dentistry control system and method can manage multiple user accounts and/or multiple patient accounts.

Any of the operations described herein that form part of the invention are useful machine operations. The invention also relates to a device or an apparatus for performing these operations. The apparatus can be specially constructed for the required purpose, such as a special purpose computer. When defined as a special purpose computer, the computer can also perform other processing, program execution or routines that are not part of the special purpose, while still being capable of operating for the special purpose. Alternatively, the operations can be processed by a general purpose computer selectively activated or configured by one or more computer programs stored in the computer memory, cache, or obtained over a network. When data is obtained over a network the data can be processed by other computers on the network, e.g. a cloud of computing resources.

The embodiments of the present invention can also be defined as a machine that transforms data from one state to another state. The data can represent an article, that can be represented as an electronic signal and electronically manipulate data. The transformed data can, in some cases, be visually depicted on a display, representing the physical object that results from the transformation of data. The transformed data can be saved to storage generally or in particular formats that enable the construction or depiction of a physical and tangible object. In some embodiments, the manipulation can be performed by a processor. In such an example, the processor thus transforms the data from one thing to another. Still further, the methods can be processed by one or more machines or processors that can be connected over a network. Each machine can transform data from one state or thing to another, and can also process data, save data to storage, transmit data over a network, display the result, or communicate the result to another machine. Computer-readable storage media, as used herein, refers to physical or tangible storage (as opposed to signals) and includes without limitation volatile and non-volatile, removable and non-removable storage media implemented in any method or technology for the tangible storage of information such as computer-readable instructions, data structures, program modules or other data.

Although method operations can be described in a specific order, it should be understood that other housekeeping operations can be performed in between operations, or operations can be adjusted so that they occur at slightly different times, or can be distributed in a system which allows the occurrence of the processing operations at various intervals associated with the processing, as long as the processing of the overlay operations are performed in the desired way.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto.

The invention claimed is:

1. A dental apparatus control system comprising:
at least one computer system including at least one processor, the at least one computer system configurable to control at least one function of a dental apparatus;
at least one user display configured and arranged to exchange information with the at least one controller, the at least one user display including at least one graphical user interface;
a non-transitory computer-readable storage medium configured to tangibly store thereon program logic for execution by the at least one processor, the program logic including a dental apparatus control system that when executed by the at least one processor, is configured to update the at least one graphical user interface by:
rendering a first display adjacent a second display, both the first display and the second display comprising at least one user-selectable segment; and
rendering at least one menu portion adjacent the at least one user-selectable segment, the at least one menu navigation portion including displayed information related to any user-actuable function represented by any one of the user-selectable segments, and
wherein following selection of a segment by a user through interaction with graphical user interface, the at least one processor is configured by the program logic to render the segment with a distinguishing graphical look, and is further configured to initiate a control sequence accessing or controlling one or more of the functions of the dental apparatus.

2. The control system of claim 1, wherein upon initiating the control sequence based on the selected segment, the at least one processor is configured by the program logic to receive data from the dental apparatus indicative of a status or operation of the dental apparatus, and is further configured to provide an icon or graphical update within the at least one graphical user interface based at least in part on at least a portion of the received data.

3. The control system of claim 1, wherein the second display extends along at least a portion of the first display.

4. The control system of claim 1, wherein the second display includes at least one banner associated with a segment, the at least one banner comprising a notification or description of a parameter or function represented by the segment.

5. The control system of claim 1, wherein the at least one menu navigation portion includes at least one section configured to provide information related to at least one sub-menu.

6. The control system of claim 1, wherein the graphical user interface further comprises a display of a recommendation for one or more accessories of the dental apparatus.

7. The control system of claim 1, wherein the processor is further configured by the program logic to display associative icons that relate to dental categories, dental procedures, dental steps, or options.

8. The control system of claim 1, wherein the processor is further configured by the program logic to display at least one of video and graphics related to a user help guide.

9. The control system of claim 1, wherein the second display comprises at least one of a user-selectable dental treatment category and user-selectable dental procedure.

10. The control system of claim 1, wherein the second display comprises one or more selectable steps or options of a dental procedure represented as the at least one of the user-selectable segment.

11. The control system of claim 1, wherein the first display includes a display of one or more parameters of any user-selected step of a dental procedure.

12. The control system of claim 1, wherein the processor is further configured by the program logic to display a parameter display indicating one or more parameters of the dental apparatus station.

13. The control system of claim 1, wherein the parameter display includes a display of a percentage of a substance used during a dental procedure performed by the dental apparatus.

14. The control system of claim 1, wherein the second display comprises at least one user-defined or selected favorite dental procedures or favorite steps of a dental procedure represented as at least one of the at least one user-selectable segments.

15. The control system of claim 1, wherein the selection of the at least one user-selectable segment occurs based on a user's touch of the user display of a segment.

16. A non-transitory storage medium comprising:
a non-transitory computer-readable storage medium configured to tangibly store thereon program logic for execution by at least one processor, the program logic including a dental apparatus control system that when executed by the at least one processor, is configured to display or update at least one user interface by:
displaying at least a portion of a graphical user interface on at least one user display, the at least one user display configured and arranged to exchange information with at least one dental apparatus controller;
rendering on the graphical user interface a first display adjacent a second display, the second display comprising at least one user-selectable segment; and
rendering on the graphical user interface at least one menu portion adjacent the at least one user-selectable segment, the at least one menu navigation portion including displayed information related to any user-actuable function represented by any one of the user-selectable segments, and
wherein following selection of a segment by a user through interaction with graphical user interface, the at least one processor is configured by the program logic to render the segment with a distinguishing graphical look and is further configured to initiate a control sequence accessing or controlling one or more of the functions of the dental apparatus.

17. The non-transitory storage medium of claim 16, wherein the processor is further configured by the program logic to display a percentage of a substance used in the dental procedure.

18. The non-transitory storage medium of claim 16, wherein the processor is further configured by the program logic to display associative icons that relate to dental categories, dental procedures, dental steps, or options.

* * * * *